(12) United States Patent
Elliott et al.

(10) Patent No.: US 8,580,248 B2
(45) Date of Patent: Nov. 12, 2013

(54) CULTURE AND USE OF CELLS THAT SECRETE LIVER SECRETORY FACTORS

(75) Inventors: Robert Bartlett Elliott, Auckland (NZ); Olga Garkavenko, Manukau (NZ); Alfred Vasconcellos, Cranston, RI (US); Dwaine Emerich, N. Scituate, RI (US); Chris Thanos, Cumberland, RI (US)

(73) Assignee: Fac8Cell Pty Limited, Sydney (AU)

( * ) Notice: Subject to any disclaimer, the term of this patent is extended or adjusted under 35 U.S.C. 154(b) by 1089 days.

(21) Appl. No.: 10/599,518

(22) PCT Filed: Mar. 30, 2005

(86) PCT No.: PCT/IB2005/001324
§ 371 (c)(1),
(2), (4) Date: Nov. 16, 2007

(87) PCT Pub. No.: WO2005/094162
PCT Pub. Date: Oct. 13, 2005

(65) Prior Publication Data
US 2008/0181924 A1    Jul. 31, 2008

(30) Foreign Application Priority Data

Mar. 30, 2004 (NZ) ........................ 532057
Mar. 30, 2004 (NZ) ........................ 532059
Sep. 3, 2004 (NZ) ........................ 535131

(51) Int. Cl.
*C12N 5/07* (2010.01)
*A61K 9/48* (2006.01)
*A61K 9/26* (2006.01)

(52) U.S. Cl.
USPC .......... 424/93.7; 424/422; 424/451; 424/484; 435/325; 435/347

(58) Field of Classification Search
USPC ................. 424/93.7, 422, 451, 484
See application file for complete search history.

(56) References Cited

U.S. PATENT DOCUMENTS 5,759,830 A * 6/1998 Vacanti et al. ............ 435/180
2002/0012653 A1 1/2002 Pang et al.
2003/0096411 A1 5/2003 Michalopoulos et al.

FOREIGN PATENT DOCUMENTS

WO    WO 96/40872    12/1996

OTHER PUBLICATIONS

Kobayashi et al. Primary culture of human gallbladder epithelial cells. Gastroenterol. Jpn. 1991;26:363-369.*
Clement et al. Long-Term Co-Cultures of Adult Human Hepatocytes with Rat Liver Epithelial Cells: Modulation of Albumin Secretion and Accumulation of Extracellular Material. Hepatology. 1984. vol. 4, No. 3, pp. 373-380.*
Lee et al. Cultured gallbladder epithelial cells synthesize apolipoproteins A-I and E. Am J Physiol Gastrointest Liver Physiol 285: G630-G641, 2003.*
Kobayashi et al. A reversibly immortalized human hepatocyte cell line as a source of hepatocyte-based biological support. Addiction Biology, vol. 6, Issue 4 Sep. 2001 , pp. 293-300 (abstract only; p. 1-2).*
EP Examination Report, Dec. 10, 2008 in corresponding European application (EP 05735340.1).
Australian Examination Report in corresponding Australian application (AU 2005227725), 2009.
Ferrini, et al., "Long-Term Primary Cultures of Adult Human Hepatocytes", Chemico-Biological Interactions, 1997, pp. 31-45, vol. 107, Elsevier Science Ireland Ltd.
Garcia-Martin, et al., "Therapeutic Levels of Human Factor VIII in Mice Implanted with Encapsulated Cells: Potential for Gene Therapy of Haemophilia A", The Journal of Gene Medicine, 2002, pp. 215-223, vol. 4, John Wiley & Sons, Ltd.
Hortelano, et al., "Sustained and Therapeutic Delivery of Factor IX in Nude Haemophila B Mice by Encapsulated C2C12 Myoblasts: Concurrent Tumourigenesis", Haemophilia, 2001, pp. 207-214, vol. 7, Blackwell Science Ltd.
Alison et al. (Feb. 2004) "Hepatic Stem Cells: From Inside and Outside the Liver," *Cell Prolif.* 37:1-21.
Auth, M.K.H. (Apr. 2005) "Preservation of Synthetic and Metabolic Capacity of Isolated Transplantation," 11(4):410-419.
Fausto et al. (2003) "The Role of Hepatocytes and Oval Cells in Liver Regeneration and Repopulation," *Mech. Dev.* 120:117-130.
Kurash et al. (Jan. 2004) "Induction and Regulation of Acute Phase Proteins in Transdifferentiated Hepatocytes," *Exp. Cell Res.* 292:342-358.
Lardon et al. (Jun. 2004) "Plasticity in the Adult Rat Pancreas: Transdifferentiation of Exocrine to Hepatocyte-Like Cells in Primary Culture," *Hepatology* 39(6):1499-1507.
Lim et al. (2002) "Modulation of Cyotokeratin Expression During in Vitro Cultivation of Human Hepatic Stellate Cells, Evidence of Transdifferentiation from Epithelial to Mesenchymal Phenotype," *Histochem. Cell Biol.* 118:127-136.
Masson et al. (2004) "Potential of Hematopoietic Stem Cell Therapy in Hepatology: A Critical Review," *Stem Cells* 22:897-907.
Min et al. (Mar. (2004) "Prospects for Cell-Based Therapies for Liver Disease," *Panminerva Medica* 46(1):43-48.
Shen et al. (Dec. 2000) "Molecular Basis of Transdifferentiation of Pancreas to Liver," *Nature Cell Biol.* 2:879-887.
Tosh et al. (2002) "Conversion of Pancreatic Cells to Hepatocytes," *Biochem. Soc. Trans.* 30(2):51-55.
Tosh et al. (2002) "Differentiated Properties of Hepatocytes Induced from Pancreatic Cells," *Hepatology* 36(3):534-543.

(Continued)

*Primary Examiner* — Taeyoon Kim
(74) *Attorney, Agent, or Firm* — Lathrop & Gage LLP

(57) ABSTRACT

The invention relates to an improved method of culturing hepatocyte cells and non-hepatocyte cells that are capable of secreting liver secretory factors and their use in implantable compositions for treating liver diseases and disorders in patients in need thereof.

27 Claims, 9 Drawing Sheets

(56) References Cited

OTHER PUBLICATIONS

Yamazaki et al. (2003) "Sera from Liver Failure Patients and a Demethylating Agent Stimulate Transdifferentiation of Murine Bone Marrow Cells into Hepatocytes in Coculture with Nonparenchymal Liver Cells," *J. Hepatol.* 39:17-23.

Australian Examination Report, Aug. 25, 2010 in a related Australian application (AU 2006237681).

Translation of Office Action in related Chinese Application (CN 20050017708.7), Jul. 11, 2007.

Further Office Action, Feb. 24, 2010 in a related European application (EP 05735340.1), 3pp.

Second Office Action in related Chinese Application (CN 20050017708.7), Jun. 30, 2010, 2pp.

Response to Office Action in Chinese Application (CN 20050017708.7), Jul. 27, 2010, 2 pp.

Response to Office Action of Feb. 24, 2010 in European Application (EP 05735340.1), Aug. 17, 2010, 5 pp.

Claims as amended in European Application (EP 05735340.1), Aug. 17, 2010, 5 pp.

* cited by examiner

Albumin Production

|          | Day 5 | Day 7 | Day 10 | Day 13 | Day 32 | Day 54 |
|----------|-------|-------|--------|--------|--------|--------|
| ARF+FBS  | 1.3   | 0     | 0      | 0      | 2.9    | 0      |
| ARF+PS   | 1.6   | 3.3   | 19.5   | 4.2    | 15.7   | 7.9    |
| ARF NO S | 3.9   | 0     | 0      | 0      | 0      | 0      |
| COLL+PS  | 21.2  | 2.33  | 5.06   | 6.5    | 38.2   | 3.42   |
| C+PS+F   | 2     | 1.2   | 2.48   | 1.16   | 3.76   | 0      |
| C+PS+S   | 3.3   | 1.34  | 4.34   | 4.56   | 0.36   | 0      |

| | Week 1 | Week 2 | Week 3 |
|---|---|---|---|
| ■ F+PS | 0.48 | 0 | 0.67 |
| □ Hep+PS | 1.3 | 2.6 | 0 |
| □ Hep+FBS | 1 | 0 | 0.55 |

US 8,580,248 B2

CULTURE AND USE OF CELLS THAT SECRETE LIVER SECRETORY FACTORS

CROSS REFERENCE TO RELATED APPLICATIONS

This application is a National Stage (371) of International Application No. PCT/IB2005/001324, filed Mar. 30, 2005, which claims priority to New Zealand Patent Application 532057, filed Mar. 30, 2004, New Zealand Patent Application 532059, filed Mar. 30, 2004, and New Zealand Patent Application 535131, filed Sep. 3, 2004.

TECHNICAL FIELD

The invention relates to the culture and use of cells that secrete Factor VIII and other liver secretory factors for the treatment of diseases associated with a deficiency in one, or more liver secreted factors and/or a deficiency in liver function.

Using the methods described herein, isolated cells retain the capacity to secrete Factor VIII and other liver secretory factors for extended periods of time and thus may have a wide range of applications, including, but not limited to, their use to augment, replace and/or reconstitute a functionally deficient liver by, for example, implantation.

BACKGROUND OF THE INVENTION

Many diseases, deficiencies and conditions can be treated by supplying to the patient one or more biologically active factors produced and/or secreted by living cells. In many cases, these factors can restore or compensate for the impairment or loss of organ or tissue function.

However, the impairment or loss of organ or tissue function may result in the loss of multiple metabolic functions. For example, it has been reported that in fulminant hepatic failure, liver tissue is rendered incapable of removing toxins, excreting the products of cell metabolism, and secreting essential factors, such as albumin and Factor VIII (Bontempo, et al., Blood, 69, pp. 1721-1724 (1987)).

In many diseases or conditions, the affected organ or tissue is one which normally functions in a manner responsive to the physiological state, by, for example, responding to fluctuations in the levels of specific metabolites and/or physiologically important substances, thereby maintaining homeostasis. Traditional factor supplementation therapy cannot compensate for the responsiveness of the normal tissue to these fluctuations and failure to provide such attuned responsiveness to the physiological state may lead to complications of the disease state.

Accordingly, many investigators have attempted to reconstitute organ or tissue function by transplanting whole organs or organ tissue to provide secreted products or effect metabolic functions. For example, liver transplantation is the established therapy for end-stage liver disease, as described by Starzl, et al., N. Eng. J. Med. 321:1014-1022 (1989). In another example, patients with hemophilia A have undergone liver transplantation as a result of liver failure resulting from hepatitis acquired from the blood derived factor VIII. In these instances, there has been a complete cure of the hemophilia. However, transplantation therapy is limited in its application by the scarcity of organs available for transplantation. For example, it has been reported that more than 25,000 people die each year in the United States of liver disease (Murphy, S L. Deaths: final data for 1998. Natl. Vital Stats. Rep. 2000; 48:1-105), and 11% of those listed for transplantation in 2001 died while waiting for an organ (Annual report of the U.S. Organ Procurement and Transplant Network and the Scientific Registry of Transplant Recipients, 2003).

In general, the patient must undergo immunosuppression or immunomodulation in order to avert immunological rejection of the transplant, which results in loss of transplant function and eventual necrosis of the transplanted organ or tissue. However, immunosuppressive or immunomodulatory therapy generally impairs the patient's overall immunological defences, which may increase susceptibility to the risks of a variety of serious complications, including nephrotoxicity, neurotoxicity, hypertension, increased susceptibility to infection and osteoporosis. Moreover, this approach is not always effective in altering the course and incidence of rejection episodes. Typically, the transplant must remain functional for a long period of time, even for the remainder of the patient's lifetime. It is both undesirable and expensive to maintain a patient in an immunosuppressed or immunomodulated state for a substantial period of time.

Transplanted cells may provide greater potential for treating various diseases as such cells can provide factors to replace or supplement natural factors which, due to their insufficiency or absence, cause disease. Cell implantation therapy has an advantage over traditional factor-supplementation therapy regimens as the transplanted cells can respond to fluctuations in the levels of specific metabolites and/or physiologically important substances in the recipient. The release of therapeutic factors from the transplanted cells may be properly regulated provided the transplanted cells have the necessary receptors and ability to respond to endogenous regulators.

Cell implantation therapy has an advantage over traditional organ transplantation therapies in that the availability of cells suitable for implantation is not limited as are suitable organs from cadaveric or live organ donors.

In addition, whilst cells which are to be implanted may be foreign to the host, various methods have been developed to prevent the host immune system from attacking and thereby causing the death of the implanted cells, such as, for example, placing cells in devices that provide a physical barrier between the cells and the host's immune system.

However, the isolation and culture of hepatocytes for implantation to secrete Factor VIII and other liver secretory factors, is difficult as hepatocytes are easily damaged and difficult to culture. Their long term culture and efficacy once implanted are therefore not fully characterised.

It would therefore be desirable to have a method for the long term culture of hepatocytes and other non-hepatocytes which are capable upon implantation into a patient, of secreting liver secretory factors, whereby the method results in robust cells which are suitable for long term implantation. It would also be desirable to have a method for producing Factor VIII and other liver secretory factors from cells other than hepatocytes and which are suitable for implantation in a patient in need thereof.

It is an object of the invention to go some way towards achieving these desiderata and/or to provide the public with useful choice.

STATEMENTS OF THE INVENTION

In a first aspect the present invention provides a method for the long term culture of hepatocyte cells comprising the steps:
  comminuting hepatocyte tissue in cold DMEM and incubating for up to 24 hours at 4° C.;
  twice digesting with liberase® at a concentration of 0.2 mg/ml in the presence of lignocaine;

separating the digested hepatocyte cells; and
culturing in media comprising allogeneic serum.

Preferably the hepatocytes are neonatal hepatocytes.

In a second embodiment, the present invention provides a method for the long term culture of at least one or more non-hepatocyte cell type capable of secreting one or more liver secretory factors, said method comprising the steps:

comminuting non-hepatocyte tissue in cold DMEM and incubating for up to 24 hours at 4° C.;
twice digesting with liberase® (0.2 mg/ml) for up to 10 minutes in the presence of lignocaine;
separating the digested non-hepatocyte cells; and
culturing in media comprising allogeneic serum, wherein said at least one non-hepatocyte cell type is selected from the group consisting of gall bladder epithelial cells, gall bladder endothelial cells, bile duct epithelial cells, bile duct endothelial cells, hepatic vessel epithelial cells, hepaticn vessel endothelial cells, sinusoid cells and non-parenchymal liver cells.

Optionally, the method further includes the step of co-culturing the non-hepatocyte cells with hepatocytes.

Preferably, the non-hepatocyte cells, and hepatocyte cells when used, are neonatal cells.

The one or more liver secretory factors may include albumin, blood clotting factors such as factor VIII or factor IX, growth and/or differentiation factors such as growth hormone and analogues thereof, insulin-like growth factor and analogues thereof, hepatocyte growth factor and analogue thereof, or fibroblast growth factor and analogues thereof; or hormones such as corticosteroids.

The co-culturing of non-hepatocyte cells with hepatocytes helps to maintain the phenotype of each cell type.

According to a further aspect, the invention provides a method of producing one or more liver secretory factors in vitro from at least one non-hepatocyte cell type selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells, said method comprising the steps of:

isolating said at least one non-hepatocyte cell type;
culturing said at least one non-hepatocyte cell type in media supplemented with allogeneic serum for a time sufficient to allow secretion of said one or more liver secretory factors into the media;
harvesting said media; and
optionally isolating or purifying said liver secretory factors.

Optionally, the at least one non-hepatocyte cell type may be co-cultured with hepatocyte cells.

Preferably said at least one non-hepatocyte cell type and/or hepatocyte is isolated from neonatal tissue.

According to a further aspect of the invention there is provided an implantable composition comprising at least one non-hepatocyte cell type capable upon implantation into a recipient of secreting one or more liver secretory factors or of providing one or more liver metabolic and/or physiologic functions to said recipient, wherein said one or more non-hepatocyte cell type is selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells.

Optionally, the composition further comprises hepatocyte cells.

Preferably the at least one non-hepatocyte cell type and/or hepatocyte cells are neonatal cells.

According to a further aspect of the invention, there is provided a method of producing one or more liver secretory factors in vivo, comprising the step of implanting the compositions of the invention into a patient in need thereof.

Preferably said composition provides liver secretory factors or provides liver metabolic or physiologic functions over an extended period post implantation According to a further aspect of the invention there is provided an implantable composition comprising one or more aggregates of at least one non-hepatocyte cell type capable upon implantation into a recipient, of producing and/or secreting one or more liver secretory factors, wherein said at least one non-hepatocyte cell type is selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells.

Optionally, the aggregates further comprise hepatocyte cells.

Preferably, the at least one non-hepatocyte cell type and/or hepatocyte cells used in the methods and compositions of the invention are pig or human cells.

Preferably, the at least one non-hepatocyte cell type and/or hepatocyte cells used in the methods and compositions of the invention are neonatal pig or human cells.

Where the invention comprises the use of hepatocyte cells, the hepatocytes may be isolated from commercial cell cultures of immortalised or non-immortalised cell cultures such as those available from Cell Dynamics LLC (Smyrna, Ga., USA), or may be cultured according to the method described above.

The at least one non-hepatocyte cell type is preferably gall bladder cells, most preferably gall bladder endothelial and/or epithelial cells.

The invention is preferably directed to compositions comprising gall bladder epithelial cells and hepatocytes in a ratio of between 0.5:2 and 2:0.5, preferably 1:1.

In one embodiment, the one or more liver secretory factors is a blood clotting factor.

Preferably the blood clotting factor is Factor VIII, or Factor IX.

Alternatively, the blood clotting factor is both Factor VIII and IX.

When the blood clotting factor is Factor VIII, von Willebrand factor is also secreted and, more preferably, von Willebrand factor is associated and/or complexed with said Factor VIII.

In another embodiment, the one or more liver secretory factors is a growth and/or differentiation factor.

Preferably the growth and/or differentiation factor is selected from growth hormone and analogues thereof, insulin like growth factor and analogues thereof, hepatocyte growth factor and analogues thereof, or fibroblast growth factor and analogues thereof.

In another embodiment, the one or more liver secretory factors is an enzyme.

In one embodiment, said non-hepatocyte cell types are derived from the same species as the recipient.

According to a further aspect of the invention there is provided a method of treating a patient suffering from or predisposed to a disease or condition associated with a deficiency in or absence of a liver secreted factor comprising the implantation of an effective amount of one or more implantable compositions of the invention, to a patient in need thereof.

Preferably, said one or more implantable compositions comprise gall bladder epithelial cells and hepatocytes in a ratio between 0.5:2 to 2:0.5, preferably in a ratio of 1:1.

Preferably, said disease or condition is chronic liver insufficiency, liver failure, liver disease, or alcoholic liver disease.

In one embodiment, said insufficiency, failure or disease is caused by infection, and in particular, infection with hepatitis A or B virus.

According to a further aspect of the invention there is provided a method of treating a patient suffering from or predisposed to a blood clotting disease or condition comprising the implantation of an effective amount of one or more implantable compositions of the invention to a patient in need thereof.

According to a further aspect of the invention there is provided a method of treating a patient suffering from or predisposed to hemophilia and/or a blood-clotting disease or disorder comprising the implantation of an effective amount of one or more implantable compositions of the invention to a patient in need thereof.

Preferably said hemophilia is hemophilia A.

Preferably said implantable composition comprises pig or human cells.

Preferably said implantable composition comprises neonatal cells.

Preferably, the implantable composition of the invention, comprises cells encapsulated in a suitable biocompatible material (such as alginate);

cells confined in a suitable device (such as a vascularized tube or Theracyte™ device);

cells encapsulated in matrix preparations such as gelatin, collagen, and/or natural carbohydrate polymers; and/or cells confined in a plasma thrombin clot including allogeneic plasma clots produced with allogeneic thrombin.

According to another aspect of the invention there is provided a method of administering a blood clotting factor to a patient in need thereof, wherein said blood clotting factor is complexed and/or associated with one or more factors capable of enhancing the activity, stability, bioavailability, and/or efficacy of said blood clotting factor, wherein the method comprises the implantation of an effective amount of one or more implantable compositions of the invention to said patient.

The implantable composition may comprise pig or human cells.

The implantable composition may comprise neonatal cells.

Preferably said blood clotting factor is Factor VIII, more preferably said blood clotting factor is Factor VIII and said one or more factors capable of enhancing the activity, stability, bioavailability, and/or efficacy of said blood clotting factor is von Willebrand factor.

According to a further aspect of the invention there is provided a method of treating a patient suffering from or predisposed to a disease or condition associated with a deficiency in a metabolic and/or physiologic function of the liver, said method comprising the implantation of an effective amount of one or more implantable compositions of the invention to the patient.

Preferably the composition comprises pig or human cells.

Preferably the composition comprises neonatal cells.

The disease or condition may comprise chronic liver insufficiency, liver failure, liver disease, or alcoholic liver disease.

In one embodiment, said insufficiency, failure or disease is caused by infection, and in particular, infection with hepatitis A or B virus.

According to a further aspect of the invention there is provided a use of at least one non-hepatocyte cell type selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells in the manufacture of a medicament for treating a patient suffering from or predisposed to a disease or condition associated with a deficiency in or absence of a liver secreted factor.

Preferably, said medicament further comprises hepatocytes. More preferably, the medicament comprises an implantable composition comprising gall bladder epithelial cells and hepatocytes in a ratio between 0.5:2 to 2.0.5, preferably in a ratio of 1:1.

Preferably, said disease or condition is chronic liver insufficiency, liver failure, liver disease, or alcoholic liver disease.

In one embodiment, said insufficiency, failure or disease is caused by infection, and in particular, infection with hepatitis A or B virus.

According to a further aspect of the invention there is provided a use of at least one non-hepatocyte cell type selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells in the manufacture of a medicament for treating a patient suffering from or predisposed to a blood clotting disease or condition, such as hemophilia, and in particular, hemophilia A.

According to a further aspect of the invention there is provided a use of at least one non-hepatocyte cell type selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells for treating a patient suffering from or predisposed to a disease or condition associated with a deficiency in a metabolic and/or physiologic function of the liver.

The disease or condition may comprise chronic liver insufficiency, liver failure, liver disease, or alcoholic liver disease.

In one embodiment, said insufficiency, failure or disease is caused by infection, and in particular, infection with hepatitis A or B virus.

Preferably said medicament described herein is an implantable composition and comprises pig or human cells.

Preferably said medicament comprises neonatal cells.

Preferably, the medicament comprises cells encapsulated in a suitable biocompatible material (such as alginate);

cells confined in a suitable device (such as a vascularized tube or Theracyte™ device);

cells encapsulated in matrix preparations such as gelatin, collagen, and/or natural carbohydrate polymers; and/or cells confined in a plasma thrombin clot including allogeneic plasma clots produced with allogeneic thrombin.

According to yet a further aspect of the invention there is provided a device for implantation into a recipient suffering from or predisposed to a disease associated with a deficiency in or absence of a secreted liver factor, the device comprising one or more implantable compositions of the invention.

Said disease may comprise a blood-clotting disease or disorder, such as hemophilia.

The device may comprise pig or human cells.

The device may comprise neonatal cells.

The device may comprise:

a capsule comprising a suitable biocompatible material (such as alginate);

a vascularized tube or chamber, more preferably a TheraCyte™ device available from TheraCyte, Inc., CA;

a matrix preparation comprising gelatin, collagen, and/or natural carbohydrate polymers; or a plasma thrombin clot including an allogeneic plasma clot produced with allogencic thrombin.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

DETAILED DESCRIPTION

Figure 1:
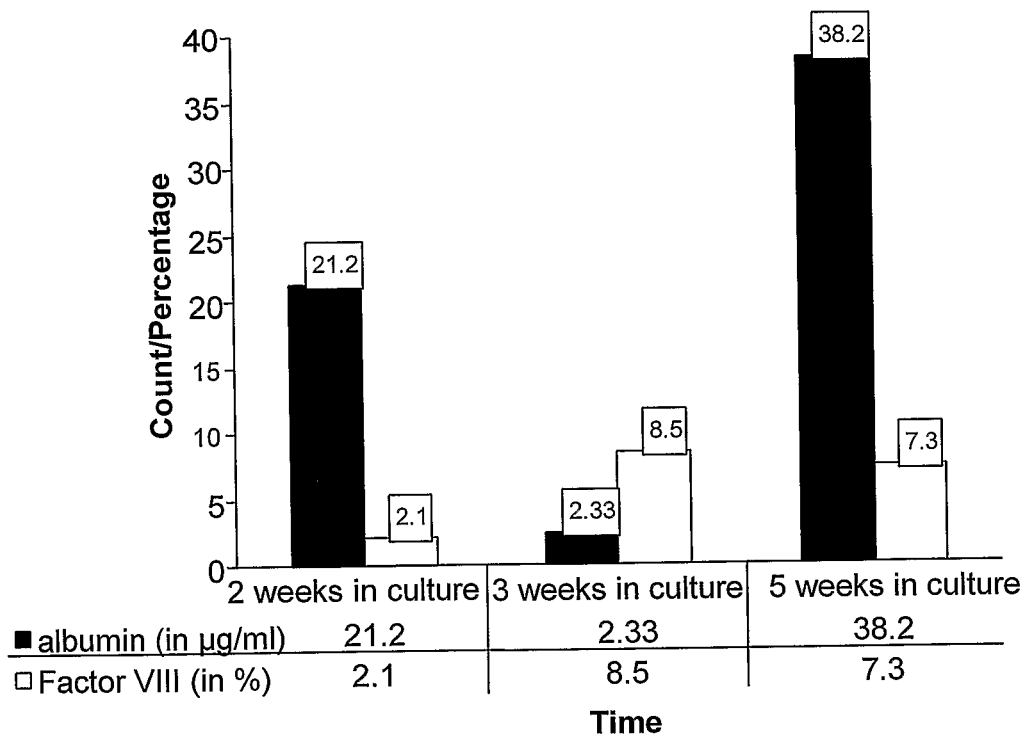
FIG. 1 depicts a graph of factor VIII and albumin production by a hepatocyte preparation as described in Example 1 herein.

It has surprisingly been found for the first time that non-hepatocyte cells are capable of secreting liver secretory factors. More specifically, non-hepatocyte cells selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells have been found to be capable of secreting liver cell factors in vitro. It is expected that such cells when transplanted to a host in vivo would also produce the liver secretory factors and may be useful in treating liver diseases and disorders associated with a reduced liver secretory function. The invention also contemplates the use of at least one non-hepatocyte cell type capable of secreting liver secretory factors in combination with hepatocytes in compositions for implanting into human hosts to treat liver diseases and disorders.

It has also surprisingly been found that hepatocytes and non-hepatocyte cells capable of secreting liver secretory factors may be isolated using a cold ischemia step to produce more robust and viable cells which are capable of producing Factor VIII and other liver secretory factors in long term culture. Such cells are then suitable for incorporation into an implantable device for implantation into patients to treat liver disease and disorders.

The methods, compositions and devices of the present invention are useful for long-term, physiologically-responsive provision of a wide range of biologically active liver secretory factors to an individual in need thereof and/or to provide needed liver metabolic and/or physiologic functions to an individual in need thereof. Biologically active factors used in the methods of the invention include a wide variety of molecules normally secreted by the liver. For example, Factor VIII can be delivered to a Type A hemophiliac, or α1-antitrypsin can be delivered to a patient with α1-antitrypsin deficiency.

The methods, compositions and devices described herein can also be used to restore or augment vital liver-mediated metabolic and/or physiologic functions, such as the removal of toxins or harmful metabolites (e.g., cholesterol) from the bloodstream by the at least one non-hepatocyte cell type, which, surprisingly show hepatocyte-like characteristics. Specifically, the at least one nonhepatocyte cell type is selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells. The compositions and devices of the invention make possible the implantation of cells without the concomitant need to immunosuppress the recipient for the duration of treatment. Through use of the methods, compositions and devices of this invention, homeostasis of particular substances and/or metabolic and/or physiologic function can be restored and maintained for extended periods of time.

Loss of or reduction in liver function is responsible for a great number of diseases, conditions and deficiencies. For example, inborn errors of metabolism relating to the liver individually are rare but collectively are common. The biological basis of the majority of inborn errors of metabolism relating to the liver is single gene defects, which result in abnormalities in the synthesis or catabolism of proteins, carbohydrates, or fats. Most inborn errors of metabolism relating to the liver are due to a defect in a biological factor, such as an enzyme or protein, which leads to a block in a metabolic pathway. Pathophysiological effects most commonly result from toxic accumulations of substrates before the block, accumulation of intermediates from alternative metabolic pathways, and/or defects in energy production and utilization caused by a deficiency of products beyond the block.

For example, hemophilia A results from an inherited deficiency of clotting factor VIII, normally produced by the liver. When less that 1% of normal factor VIII activity exists in the blood, severe bleeding episodes in response to minimal trauma occur.

Hemophilia affects about 1/10,000 live births around the world. About ⅓rd of these cases are in the severe category.

The established treatment is replacement by injection of the missing FVIII. Isolated FVIII was originally derived in semipurified form from blood, and was thereby subject to the problems associated with blood-derived products, such as being a potential source of infectious agents, such as HIV, or Hepatitis B and C. Blood-derived FVIII has in part been replaced by recombinant factor VIII.

Ideally, FVIII is given prophylactically, but therapy is very expensive (about $100,000/year). Furthermore, neutralizing antibodies may be generated in the patient, inhibiting the activity of the injected factor.

Occasionally, patients with hemophilia A have undergone liver transplantation as a result of liver failure resulting from hepatitis acquired from the blood derived FVIII. In these instances, there has been a complete cure of the Hemophilia.

Examples of diseases or conditions suitable for treatment with the methods, compositions and devices of the present invention include diseases or conditions characterised by liver cell death or dysfunction including but not limited to chronic liver insufficiency, liver failure, or liver disease, for example, that caused by infection such as infection with hepatitis A or B virus, and alcoholic liver disease.

Other examples of diseases or conditions suitable for treatment with methods, compositions, devices and aggregates of the present invention include the following: diseases characterised by cell death or dysfunction including but not limited to endocrine diseases, Diabetes, congenital adrenal hyperplasia and adrenal insufficiency, Hypothyroid diseases, Hypoparathyroid diseases, Hypogonadism, Diabetes insipidus, growth hormone deficiency; disorders of imino acid metabolism including but not limited to Hyperprolinaemia, Hydroxyprolinaemia; disorders of tryptophan metabolism including but not limited to Xanthurenic aciduria, Hydroxykynureninuria, Carcinoid syndrome, Kynureninuria, Dihydropleridine reductase deficiency; disorders of the gamma glutamyl cycle including but not limited to Glutamic acid decarboxylase deficiency, Glutamate dehydrogenase deficiency, 5-oxoprolinuria (pyroglutamic aciduria), Glutathionaemia, γ-glutamyl-cysteine synthetase deficiency; Organic Acidurias including but not limited to: Methylmalonic academia, Propionic acidaemia including but not limited to: Methylcrotonyl glycinuria, Methyl-hydroxybutiric aciduria, Hydroxy-methylglutaric aciduria, Succinyl-CoA; 3-ketoacid CoA-transferase deficiency, Lactic and pyruvic acidosis, Threonine sensitive ketoacidosis including ketothiolase deficiency, Non-ketotic dicarboxylicaciduria, Caeruloplasmin deficiency (Kinnear-Wilson's disease), C'1-esterase inhibitor deficiency, transferrinaemial, 1-antitrypsin deficiency, Amyloidosis, Afibrinogenaemia; deficiencies in Blood clotting factors; Enzymopathies including but not limited to: Acutalasia, Glucose-6-phosphate dehydrogenase deficiency, Pseudocholinesterase deficiency, Hypophosphatasia; Immunoglobulin (antibody) deficiency syndrome including but not limited to: Congenital hypogammaglobulinaemias, X-linked recessive with lymphopenia and thymic alymphoplasia, X-linked recessive without lymphopenia, sporadic congenital with or without lymphopenia, Ataxia-telangiectasia syndrome, Wiskott-Aldrich syndrome, Dysgammaglobulinaemia including transient, Dysgammaglobulinaemia including congenital, Dysgammaglobulinaemia including acquired, Adenosine deaminase deficiency, Purine nucleotide phosphorylase deficiency; disorders of amino acids including: Hyper-alaninaemia; Inborn Errors of Protein Metabolism including but not limited to: Analbuminaemia, Idipathic hypoproteinaemia, Asymptomatic protein deficiencies, disorders of red cells including but not limited to: Pyruvate kinase deficiency, Hexokinase (HK) deficiency, Phosphohexose (PHI) isomerase deficiency, Triose phosphate isomerase (TPI) deficiency, 2.3 Diphossphoglycerate mutase deficiency, Phosphoglycerate kinase (PGK) deficiency, Adenosine triphosphatase (ATP-ase) deficiency, Glucose-6-phosphate dehydrogenase (G-6-PD) deficiency, Reduced glutathione deficiency, Glutathione reductase deficiency, Glutathionine peroxidase deficiency, Glutathione synthesis defect, Methaemoglobin reductase; Galactosaemia, Acatalasia, Argininosuccinic aciduria; disorders of pigment metabolism including but not limited to: Albinism, Porphyria including Congenital erythropoietic prophyria, Erythropoietic protoporphyria, Hepatic porphyria including: Acute intermittent (Swedish type) porphyria, Hereditary coproporphyria, Mixed or variegate oporphyria, Cutaneous hepatic porpyria (tarda), Hyperbilirubinaemia, Unconjugated hyperbilirubinaemia including: Glucose-6-phosphate dehydrogenase deficiency, Crigler-Najjar syndrome, Conjugated hyperbilirubinaemia including: Dubin Johnson syndrome, Rotor's disease, Methaemoglobinaemias, Haemochromatosis, Disorder of melanin pigmentation; Disorders of Purine Metabolism including but not limited to: Xanthinuria, Hyperuricaemia, Gout, Lesch-Nyhan syndrome, Secondary uricaemia; Disorders of carbohydrate metabolism including but not limited to: Galactosaemia, Galactokinase deficiency, Uridine diphosphate galctose-4-epimerase deficiency, Hereditary fructose intolerance (HFI), Fructose-1, 6-diphosphatase deficiency, Disorders of polysaccharide metabolism-glycogen storage diseases (Glycogenoses) including but not limited to: Type I—Von Gierke's disease (Hepatorenal GSD), Type Ib (Hepatorenal GSD), Type II—Pompe's disease (Generalised GSD), Type III—Cori's disease (limit dextrinosis), Type IV—Andersen's disease (Amylopectinosis), Type V—McArdle's disease, Type VI—Hers disease, Type VII—Tauri's disease, Type VIII—Huijing's disease, Glycogen synthetase deficiency (Aglycogenosis), Muscle phosphohexosisommerase deficiency; Disorders of mucopolysaccharide metabolism including but not limited to: Type I—Huler syndrome, Scheie syndrome, Hurler syndrome, Type II—Hunter syndrome, Type III—Sanfilippo Syndrome (A, B and C), Type IV—Morquio-Brailsford syndrome (A and B), Type VI—Maroteaux-Lamy syndrome, Type VII—Glucuronidase deficiency; Glycorprotein storage diseases including but not limited to Mannosidosis, Fucidosis, Aspartylgucoarninuria; disorders of amino acid metabolism including: disorders of aromatic amino acid metabolism including but not limited to: Phenykletonuria, Dihydropteridine reductase deficiency, Methylmandelic aciduria, Tyrosinaemia, tyrosyluria, tyrosinosis, Pichner-Hanhard syndrome, Albinism, Xanthism, Hermansky-Pudlak syndrome, Chediak-Higashi disease, Cross syndrome, Dysautonomia (Riley-Day syndrome); disorders of metabolism of sulphur containing amino acids (cystine; cystathione; homocystine; methionine) including Homocystinuria, Homocystinuria with methylmalonic aciduria, $N^{5.10}$Methyleneterahydrofolate reductase deficiency, Cystathonimuria, Sulphite oxidase deficiency including β-mercaptolactase-cysteine disulphiduia, Cystinuria, Cystinosis, Hypermethioninaemia, Methionine malabsorption (Oast-house syndrome); disorders associated with hyperammonaemia including but not limited to: Argininosuccinicaciduria, Citullinaemia, Hyperornithinaemia, Argininaemia, N-Acetylglutamate synthetase deficiency, Carbamyl phosphate synthetase deficiency, Ornithine transcarbamaylase deficiency, Ornithinaemia; disorders of lysine metabolism including but not limited to Hyperlysinaemia, Periodic hyperlysinaemia with hyperammonaemia, Saccharopinuria, Pipecolic acidaemia, α-Ketoadipic aciduria, Glutaric aciduria, Crotonic acidaemia, Hydroxylysinaemia, Hydroxylsinuria, Ehlers-Danlos syndrome (type VI); disorders of branched-chin amino acid metabolism including but not limited: Maple syrup urine disease, Hyperleucine-isoleucinaemia, Methylmalonic academia, Propionic acidaemia, Methylcrotonylglycinuria, α-Methyl-hydroxybutiric aciduria, Methyl glutaconic aciduria, Hydroxyl-methylglutaric aciduria, Isovalericacidaemia, Hypervalinaemia; disorders of histidine metabolism including but not limited to: Carnosinaemia, Urocanic aciduria, disorders of folic acid metabolism (cyclohydrolase and forminotransferase deficiency), Glutamate formiminotransferase deficiency, Disorders of Glycine Metabolism including but not limited to: Hyperglycinaemia, D-Glyceric acidaemia, Oxalosis, Sarcosinaemia, Trimethylaminuria; disorders of lipid metabolism including but not limited to: Hyperlipoproteinaemias including Familial hyperchylomicronaemia (Type I), Familial hyper-lipoproteinaemia (familial hypercholesterolaemia) (Type IIA), Combined hyperlipidaemia Type IIB, Broad—disease (Type III) Pre-lipoproteinaemia (Type IV), Hyperchylomicronaemia with pre-lipoproteinuria (Type V); Hypolipoproteinaemias including but not limited to: A—lipoproteinaemia (acanthocytosis), Familial (primary) hypobetalipoproteinaemia, Familial α-lipoprotein deficiency (Tangier disease), Familial lecithin-cholesterol acyltransferase deficiency LCAT); lipid storage diseases including but not limited to: Mucolipidosis Type I (lipomucopolysacchariodosis), Mucolipidosis Type II (I cell disease), Mucolipidosis Type III (pseudo Hurler polydystrophy), GM1 generalised gangliosidosis, GM1 juvenile gangliosidosis, GM2 gangliosidosis with hexosaminidase A deficiency (Tay Sachs disease), GM2 gangliosidosis with hexosamindase A and B deficiency (Sandhoff disease), Niemann-Pick disease (sphingomyelin lipidosis), Metachromatic leucodystrophy (sulphatide lipidosis), Gaucher's disease (cerebroside lipidosis), Fabry's disease (ceremide trihexoside lipidosis), Acid esterase deficiency (Wolman's disease); disorders of calcium, phosphorus, magnesium and other minerals including but not limited to: Hypercalcaemic states including: Thyrocalcitonin deficiency, Vitamin D-resistant (hypelphosphaturic) rickets; Vitamin D-dependent rickets; Deficiency or excess of other minerals such as Copper, for example Wilson's disease; Menkes steely hair syndrome; Iron, for example, Atransferrinaemia, Haemochromatosis, Congenitall iron overload, Zinc, for example, Acrodermatitis enteropathica; and the like.

As with many diseases of other organs, liver transplantation is often a preferred therapy in diseases associated with errors of liver metabolism. For example, liver transplantation is the established therapy for end-stage liver disease. However, as with most other transplant therapies, liver transplantation is limited by the scarcity of suitable donor organs.

The transplantation of hepatocytes has been proposed as an alternative to whole organ transplantation for liver disease (Asonuma, et al, J. Ped. Surg., 27:298-301 (1992)). The authors report that single metabolic deficiencies may be cured with replacement of 12% of liver mass, suggesting a single liver could be utilized for several patients, or partial resection of a living donor's liver could provide the necessary liver mass to treat another person.

The ability of transplanted cells to manufacture and secrete substances of therapeutic value, or provide needed metabolic functions, and so potentially provide an alternative to whole organ transplantation, has led to the development of implantable devices for maintaining cells within an individual in need of treatment.

In order to replace or augment liver function utilizing liver cell transplantation, regardless of the means of cell delivery, it is critical to ensure the survival and growth of the transplanted cells. Previous studies on hepatocyte transplantation have reported that performing a portal caval shunt (PCS) in conjunction with hepatocyte transplantation improves hepatocyte engraftment (Uyama, et al., Transplantation 55:932-935 (1993)). However, patients in need of liver function replacement, such as hemophiliacs or patients in liver failure, are already in a compromised situation, and the burden of a PCS may not be feasible for this population.

The invention disclosed herein provides improved methods for culturing hepatocytes and further culturing at least one non-hepatocyte cell type which is capable of secreting one or more liver secretory factors and/or providing one or more liver metabolic and/or physiologic functions, when implanted into a recipient. The invention also contemplates the use of at least one non-hepatocyte cell type in combination with hepatocytes, including co-culturing of said non-hepatocyte and hepatocyte cells.

The improvement is in the use of a cold ischemia step during hepatocyte and non-hepatocyte cell isolation and results in a more robust and viable cell wherein, when cultured in media comprising allogeneic serum, is capable of secreting Factor VIII and other liver secretory factors in long term culture. Such cells are then suitable for implantation into a recipient patient for the treatment of liver diseases and disorders.

The invention thus contemplates the use of hepatocytes alone, when cultured using the improved method, in the treatment of liver diseases or disorders when implanted into a patient in need thereof. Alternatively, the invention contemplates the use of non-hepatocyte cells alone or in combination with such hepatocytes in the treatment of liver diseases and disorders.

The invention disclosed herein in respect of non-hepatocyte cells, for example, gall bladder epithelial cells, gall bladder endothelial cells, bile duct epithelial cells, bile duct endothelial cells, hepatic vessel epithelial cells, hepatic vessel endothelial cells, sinusoid cells and non-parenchymal cells relates in a preferred embodiment to the preparation and use of a composition of or a device incorporating neonatal cells, including, for example, an "aggregate" of at least one neonatal non-hepatocyte cell type, such as neonatal gall bladder cells. Alternatively, the aggregates may comprise a combination of non-hepatocyte cells and hepatocytes.

Where more than one cell type is co-cultured, for example more than one non-hepatocyte cell type, or at least one non-hepatocyte cell type and hepatocytes, the cells may interact directly for example by cell-to-cell contact, or indirectly, such as, for example, by secreted factors including hormones, cytokines, or growth and/or trophic factors. Such an interaction may be promoted and/or enhanced by the culturing of said cells in the presence of allogeneic serum.

In forming interactions between different cell types or in the formation of an aggregate, preferably comprising at least one non-hepatocyte cell type and hepatocytes, co-culturing allows the cells time to grow in the presence of growth factors produced by the cells in vitro before transplantation into a host. For example, we have found that non-hepatocyte cell secretory function and/or phenotype may be better maintained if they are cultured with and/or interact with and/or are aggregated with hepatocyte cells.

In some embodiments, the at least one non-hepatocyte cell type and, when present, the hepatocyte cells, are preferably derived from the same species as the recipient. In other embodiments, either or both of the at least one non-hepatocyte cell type and, when present, the hepatocyte cells, are from species other than that of the recipient.

We have also found that for the preparation of an aggregate comprising at least one non-hepatocyte cell type, for example, neonatal gall bladder cells, culturing in the presence of allogeneic serum allows the gall bladder cells time to grow in the presence of growth factors present in the allogeneic serum in vitro before the cells are transplanted into a recipient host.

By "aggregate" as used herein is meant a grouping of at least one non-hepatocyte cell type as defined herein, which, when implanted in to a recipient, are immunologically, but preferably not physiologically, isolated and/or privileged. An aggregate may comprise more than one non-hepatocyte cell-type. An aggregate may also comprise at least one non-hepatocyte cell type together with hepatocyte cells.

By "non-hepatocyte cell type" we mean cells from liver associated organs, including the gall bladder, bile duct and hepatic vessels, including, for example non-parenchymal liver cells, gall bladder cells including gall bladder epithelial cells and gall bladder endothelial cells, liver vessel endothelial and epithelial cells, and cells, including genetically modified cells, capable of performing metabolic or physiologic functions normally performed by the liver and/or associated organs and/or expressing and/or producing and/or secreting a biologically active molecule. Such a biologically active molecule is also referred to herein as a factor. The biologically active molecule may be selected from but not limited to one or more of the following; blood clotting factors (for example, Factor VIII, Factor IX, von Willebrand factor), growth and/or differentiation factors (for example, growth hormone and analogues thereof, insulin-like growth factor and analogues thereof, hepatocyte growth factor and analogues thereof, fibroblast growth factor and analogues thereof), and enzymes (such as glutaryl coenzyme A, the deficiency of which causes type 1 glutaric aciduria).

In preferred embodiments, said at least one non-hepatocyte cell type is a neonatal cell type.

By "neonatal" is meant of, or derived from, new-born and/or recently born mammals and/or designating or relating to the period just after birth, wherein said period varies from species to species. For instance, in humans the neonatal period is considered to be the first four weeks following birth, and for example, in pigs is considered to be the first seven to ten days following birth.

By "allogeneic serum" is meant serum suitable for cell culture derived from the same species as that from which the cells were derived. In examples of the present invention where secretory cells and companion cells from different species are co-cultured, an allogeneic serum is one derived from the same species as that from which the secretory cells were derived.

By "factor" is meant a biologically active molecule produced by a cell.

By "long term" we mean a period of more than a week, typically extended to 2-6 weeks or more.

By "extended period" is meant a period or more than a week, preferably more than two, three, four, five or six weeks or more.

Transplantation of at least one neonatal non-hepatocyte cell type, optionally with hepatocytes, has been investigated as a means of achieving long-term maintenance of liver cell phenotype and/or function, such as the capability to produce and/or secrete one or more factors and/or provide one or more metabolic and/or physiologic functions. The methods, compositions and devices, of the present invention enable neonatal non-hepatocyte cells to survive, grow, proliferate and secrete liver secretory factors when transplanted into a recipient.

Our studies described herein show that at least one non-hepatocyte cell type selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells, and in particular neonatal gall bladder cells, can, when isolated using the methods herein described, secrete one or more liver factors and/or maintain liver metabolic and/or physiologic function in vitro. Such cells survive, and indeed proliferate when cultured according to the methods herein disclosed. Furthermore, it is expected that such cells, when isolated and cultured using the methods described herein will be able to maintain cell phenotype in vivo and secretion of liver secretory factors in the long-term transplantation into a recipient.

We believe, without wishing to be bound by theory, that the isolation and/or culturing of at least one non-hepatocyte cell type and/or hepatocyte cells utilising allogeneic serum is at least in part responsible for the maintenance of cell phenotype and/or liver factor secretory function observed.

Cotransplantation of non-hepatocyte cells with hepatocyte cells is also contemplated as a means of achieving;

(a) protection against immune rejection; and (b) stimulation of survival, growth, and the mitotic rate of non-hepatocyte cells so that they release physiologically appropriate and/or effective amounts of one or more liver secretory factors, and/or maintain the capability to provide one or more metabolic and/or physiologic functions, survive longer, and/or proliferate when transplanted into a recipient.

We believe, without wishing to be bound by theory, that the provision of growth and/or trophic and/or differentiation factors and/or functions by said hepatocyte cells is at least in part responsible for the maintenance of non-hepatocyte cell phenotype, growth, survival, secretion of liver secreting factors and/or protection from immune rejection of transplanted non-hepatocyte cells.

The present invention is further directed to the use of at least one non-hepatocyte cell type, including at least one neonatal non-hepatocyte cell type, selected from the group comprising gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells, optionally with hepatocyte cells, either singly, interacting together, in aggregates or compositions in:

Alginate-encapsulated form—to provide additional immune protection of the transplanted cells. The feasibility of microencapsulating neonatal non-hepatocyte cells and transplanting same is demonstrated in Examples 5 and 6 herein. The transplantation of hepatocyte cells is demonstrated in Example 6.

Subcutaneous implant devices that allow the development of a prevascularised allogeneic collagen reservoir for the placement of the transplanted cells. Preferably, the implant device is cell impermeable but protein or secreted factor permeable, such as the "TheraCyte" device available from TheraCyte, Inc., Irvine, Calif.

Matrix preparations—in which cells to be transplanted are cultured on gelatin, collagen and/or other matrices supplemented with natural carbohydrate polymers, Plasma Thrombin Clot—Allogeneic plasma clots produced with allogeneic thrombin as a biocompatible containment device for the cells to be transplanted.

The maintenance of the secretion of liver secretory factors by hepatocytes and by at least one non-hepatocyte cell type is demonstrated herein. For instance, Example 2 herein discloses the maintenance of a secretory cell phenotype in non parenchymal cells and epithelial and endothelial cells of gall bladder and liver vessels.

Also described is the culturing of non-hepatocyte cells, and in particular gall bladder cells, in the presence of allogeneic serum. The use of media conditioned with fibroblasts or Sertoli cells (known feeder cells) which contain cell-derived factors is also disclosed. The Applicants believe, without wishing to be bound by theory, that through the provision of growth and/or trophic and/or mitogenic factors, allogeneic serum provides an enhancement of liver factor secretory function and/or a maintenance of cell phenotype and/or longevity in vitro, which may persist in vivo. Similarly, the Applicants believe, without wishing to be bound by theory, that conditioned media is able to provide an enhancement of liver factor secretory function and/or a maintenance of cell phenotype and/or longevity in vitro, which may persist in vivo.

The effects of culturing hepatocyte cells in media supplemented with allogeneic serum on the maintenance of liver cell function and enhancement of liver cell survival is demonstrated herein. For instance, Example 2 herein discloses the effect of culturing pig hepatocytes in media supplemented with porcine serum on the maintenance of a Factor VIII secretory cell phenotype.

Also described is the effect of conditioned media on the maintenance of liver cell function and enhancement of liver cell survival.

The following Examples are provided to illustrate but not to limit the invention in any manner.

EXAMPLE 1

Isolation of Liver and Gall Bladder Cells and Optimisation of Culture Conditions 1.1 Isolation of Hepatocytes Hepatocytes were isolated from neonatal porcine liver as follows. Following surgical removal, the donor livers were transferred to a clean room facility for further processing in a cold plastic container in 50 ml tubes containing cold Hank's Balanced Salt Solution (HBSS) with 0.2% human serum albumin (HSA) added. The liver cells were isolated by digestion of the minced liver via a major modification of the standard (Ricordi's) collagenase digestion procedure. Using aseptic technique, the liver was trimmed of excess fat, blood vessels and connective tissue, minced, and digested with Liberase® (0.2 mg/ml) in a shaking water bath (120 rpm) for 10 minutes. The digestion step was repeated twice. The digestion was performed using lignocaine mixed with the Liberase® solution to avoid cell damage during digestion. Following the digestion process, the cells were passed through a sterile 400 mm mesh into a sterile beaker. Following the isolation, liver cells were placed into tissue culture in various media as described herein.

1.2 Optimization of Culture Conditions

To optimise the culture conditions for survival of liver cells and the maintenance of a liver cell phenotype, different media supplemented with various additives were assessed.

Culture Media: Hepatocytes were grown in different liquid media on a number of different surfaces and on surfaces coated with different matrices. Optimum growth was found with the medium DMEM/F 12 (1:1 by volume, Invitogen Corporation, USA) supplemented with 0.5 U/ml insulin (Novo Nordisk, Denmark), 7 ng/ml glucagon (Novo Nordisk, Denmark), 7.5 µg/ml hydrocortisone (Pharmacia, USA), 1 ml/0.5 L Cyproxin 200 (Bayer, Germany)) plus, for example, the additives cyproxin, nicotinamide (10 mmol/L), and allogeneic serum (10% by volume). The best surface matrix for hepatocyte growth was found to be collagen.

1.3 Liver Cell Environment

The effect of the environment in which the liver cells were cultured on liver cell growth and function in vitro was assessed as follows.

Cell-extracellular matrix interaction: The effect of interactions between the liver cells and an extracellular matrix on cell viability and maintenance of cell-specific function in vitro was assessed using collagen as exemplary extracellular matrix.

Hepatocytes were isolated following our standard procedure. Aliquots of hepatocytes were put into a collagen-coated flask and a non-coated flask. DMEM growth media (GM) supplemented with insulin 0.5 U/mL, glucagons (7 ng/mL), hydrocortisone (7.5 ug/mL), and 10% (by volume) porcine serum (PS; Invitrogen Corporation, USA) was used. The effect of allogeneic serum supplementation on cell viability and function in the presence of a liver cell-extracellular matrix interaction was assessed, using as a control hepatocytes grown in a collegan-coated flask in growth media lacking procine serum.

Photomicrographs of the cell cultures were taken after 15 days and 18 days in culture.

At both 15 and 18 days of culturing, hepatocytes grown in the presence of a collagen extracellular matrix formed a confluent monolayer irrespective of the presence or absence allogeneic serum in the growth medium. In contrast, hepatocytes grown in the absence of a collagen extracellular matrix formed multiple foci. The functional significance of the different in vitro morphologies observed was evaluated with a test on hepatocyte function. Growth media was collected from each flask every fourth day for analysis of albumin production to check the function of hepatocytes during culture. Results for albumin production are presented in Example 2 herein.

Cell-cell interaction: Human fibroblasts were used as companion cells to study the role of cell-cell interaction in fibroblast-hepatocyte co-cultures. Growth-arrested fibroblasts and non-arrested fibroblasts were co-cultured with hepatocytes under the following experimental conditions: 700 000 non-arrested fibroblasts: 250 000 hepatocytes in GM supplemented with 10% fetal bovine serum (FBS) or 10% PS; a confluent monolayer of fibroblasts arrested with mitomycin CL 250 000 hepatocytes in GM supplemented with 10% FBS or 10% PS.

Cell morphology was assessed by photomicrography after 10, 16, 30, and 37 days in co-culture. For each cell preparation, a flask in which the cells were cultured in serum-free GM was used as a control. The effect of a 3-dimensional support structure on the cell-cell interactions was also investigated, using hepatocytes grown on nylon mesh coated with mitomycin-arrested human fibroblasts. Briefly, nylon mesh was successfully coated with human fibroblasts. The fibroblasts were then arrested with mitomycin. Hepatocytes were placed in the flask with the mesh. After 5 days the mesh was washed with fresh medium and put into a new flask.

Non-arrested fibroblasts quickly overgrew hepatocytes. Cells formed a confluent monolayer even in GM without sera. The control flask with hepatocytes grown in GM without sera was empty after 7 days in culture (data not shown), indicating these conditions could not support hepatocyte survival.

Hepatocytes grown with arrested fibroblasts in GM supplemented with 10% PS presented better morphology compared to cells in GM supplemented with 10% FBS. Cell viability as assessed by morphology was optimal after culturing for 2-3 weeks.

Optimisation of growth media: The effect of supplementation of growth media with various sera on hepatocyte growth and function was assessed. Hepatocytes (250 000 cells per flask) were grown in collagen coated flasks under the following experimental conditions: GM supplemented with 5% porcine serum (PS) and 5% Sertoli-conditioned growth media prepared as described below, GM with 5% PS and 5% pig skin fibroblast-conditioned growth media prepared as described below, and 10% PS.

Sertoli-conditioned growth media was prepared as follows: Sertoli cells were cultured for at least 24 hours before growth media was collected and filtered through an 8 micron filter to remove cells. The filtered media was then diluted in a 1:1 ratio with DMEM before use.

Pig skin fibroblast-conditioned growth media was prepared as described for Sertoli-conditioned growth media above, with the substitution of fibroblasts for Sertoli cells. The pig skin fibroblasts were isolated as follows: Pig skin was soaked in DMEM plus cyproxin, and fungizone, for 20 minutes, then cut with a scalpel into small pieces. Pieces of tissue were then placed in a standard culture flask with DMEM media supplemented with 10% PS. After one week of culture, pieces of tissue were removed, the remaining cells adhering to the flash were washed, and fresh growth medium was added.

Supplementation of growth media with 10% PS, or 5% PS and 5% pig skin fibroblast-conditioned growth media, yielded better hepatocyte viability than supplementation of growth media with 5% PS and 5% Sertoli-conditioned growth media. Cell viability as assessed by morphology was optimal after culturing for two to three weeks.

Analysis of the morphology of the cells in culture showed that for hepatocyte viability and growth in vitro, supplementation of growth media with allogeneic (porcine) serum was preferable to supplementation with foetal bovine serum. Furthermore, supplementation of growth media with either 10% PS, or 5% PS and 5% fibroblast-conditioned growth media was preferable to supplementation with 5% porcine secrum and 5% Sertoli-conditioned media.

1.4 Isolation of Non Parenchymal Liver Cells and Gall Bladder Cells

Non-parenchymal liver cells (NPC) were isolated following the procedure by Gerlach et al. (2001), with the following modifications. Briefly, the liver was cut into small pieces, and washed three times to remove erythrocytes. Tissue was then digested with Liberase® (0.2 mg/ml) for 30 min. Digestion was stopped with 10% porcine serum. Hepatocytes were sedimented at 50 g for 5 min. Non-parenchymal liver cells were sedimented at 600 g for 10 mm, and then washed three times in PBS. Cells were counted, and their viability was checked by trypan blue exclusion as described above. Cells were plated at 10,000 cells/flask. At day 7 in culture, the cell count and viability check was repeated. Supernatant was collected for albumin ELISA and Factor VIII functional tests.

10,000 NPC were isolated from the same neonatal pig liver. Viability of cells immediately after isolation was 100%. Maximal rate of Factor VIII coagulation was 0.2% at day 5 in culture.

Epithelial and endothelial cells were isolated from pig gall bladder and liver vessels. Briefly, gall bladder was thoroughly washed with sterile DMEM to remove bile, cut into pieces, and digested with Liberase® (0.2 mg/ml) for 30 min. Cells were then washed with DMEM three times. Cell count and viability tests were performed immediately after isolation, and again at day 7, day 16, and day 28 in culture. Cells were plated in 25 $cm^2$ flasks at $15 \times 10^6$ cells/flask. Albumin and FVIII release functional tests were performed at day 7 in culture.

$31 \times 10^6$ Cells were isolated from pig gall bladder and liver vessels. Viability immediately after isolation was 100%. After 16 days in culture, cell survival rate was 120%. Maximal albumin production was 2.27 ug/ml/4 h, and the maximal rate of Factor VIII coagulation was 3.7%.

EXAMPLE 2

Characterization of Cells: Secretory Function and Cell Markers

To determine whether hepatocyte cells and non-hepatocyte cells in culture maintain liver factor secretory function, the following experiments were conducted.

Albumin Secretion

Albumin is the major plasma protein secreted by hepatocytes. In conventional culture methods, the rate of secretion of albumin drops rapidly during culture. Hepatocyte albumin secretion was used herein as a test for the maintenance of normal hepatocyte function, and thus the maintenance of a liver cell phenotype, for example, in culture.

Factor VIII

The liver and the reticularendothelial system are thought to be primary sites of Factor VIII production. Liver transplant corrects Factor VIII deficiency in persons with hemophilia. Factor VIII is secreted as a glycoprotein into the circulation as a heterodimer. Factor VIII production may be used to characterise liver cells. Factor VIII present in the filtered supernatant was measured using the Dade-Behring clotting system (Coatest VIII;c/4 from Chromogenix).

2.1 Albumin and Factor VIII Production by Liver Cells

Hepatocytes isolated from neonatal porcine liver according to the protocol described above, were cultured in the preferred liquid medium for up to 5 weeks on a matrix of collagen as described above. The production of Factor VIII and albumin was then determined as follows.

250,000 hepatocytes per flask were cultured in medium supplemented with additives. Supernatant from the cultured cells was removed and discarded, and cultures were washed twice with PBS. 5 ml serum-free media was then added to the culture flasks. A 1 ml aliquot of media was immediately removed from the flask and used for a baseline measurement. Cells where then incubated at 37° C. for 4 hours. After incubation, supernatant was collected, and filtered to remove cellular debris. Albumin present in the filtered supernatant was measured using the pig albumin ELISA Core Kit (Komabiotech) following the manufacturer's protocol. Factor VIII present in the filtered supernatant was measured using the Dade-Behring clotting system.

Production of Factor VIII was observed, with cells producing considerable quantities after 2 weeks in culture and maintaining the output of Factor VIII for 5 weeks (see FIG. 1) at which time the experiment was terminated.

The output of 250,000 hepatocytes over a 4-hour period gave a Factor VIII value approximately 8% of normal blood levels. Since the half life of Factor VIII in human blood is 36 hours, this rate of production is very substantial. It should also be noted that the production of albumin by these hepatocyte preparations correlates well with Factor VIII production. Albumin is a typical liver product, and production of albumin indicates the hepatocytes were healthy.

These results indicate that neonatal hepatocytes are able to maintain a secretory liver cell phenotype during prolonged cell culturing.

In another experiment, media harvested from hepatocytes grown under the various conditions described in Example 1 above, (and reproduced below) were analysed for albumin content as a determinant of hepatocyte function.

1—Hepatocytes on mitomycin arrested fibroblasts in growth media supplemented with 10% FBS:
2—Hepatocytes on mitomycin arrested fibroblasts in growth media supplemented with 10% PS;
3—Hepatocytes on mitomycin arrested fibroblasts in grown media without serum, see;
4—Hepatocytes on collagen coat in growth media supplemented with 10% PS;
5—Hepatocytes on collagen coat in growth media supplemented with 5% PS and 5% fibroblast conditioned growth media;
6—Hepatocytes on collagen coat in growth media supplemented with 5% PS and 5% Sertoli conditioned cells growth media.

Albumin content was analysed as follows: Aliquots of supernatant were taken at day 5, 7, 10, 13, 32 and 54 of culture. First, supernatant from the cultured cells was removed and discarded, and cultures were washed with PBS. 5 ml of growth media without serum was then added. A 1 ml aliquot of this growth media was immediately taken from the flask, and used for a baseline measurement of albumin production. Cells were then incubated at 37° C. for four hours. After incubation, supernatant was collected and filtered to remove cellular debris. Albumin present in the filtered supernatant was measured using pig albumin ELISA Core Kit (Komabiotech) according to the manufacturer's protocol. Growth media prepared in accordance with the original culture conditions was then added to the flasks for continued culturing.

Figure 2:
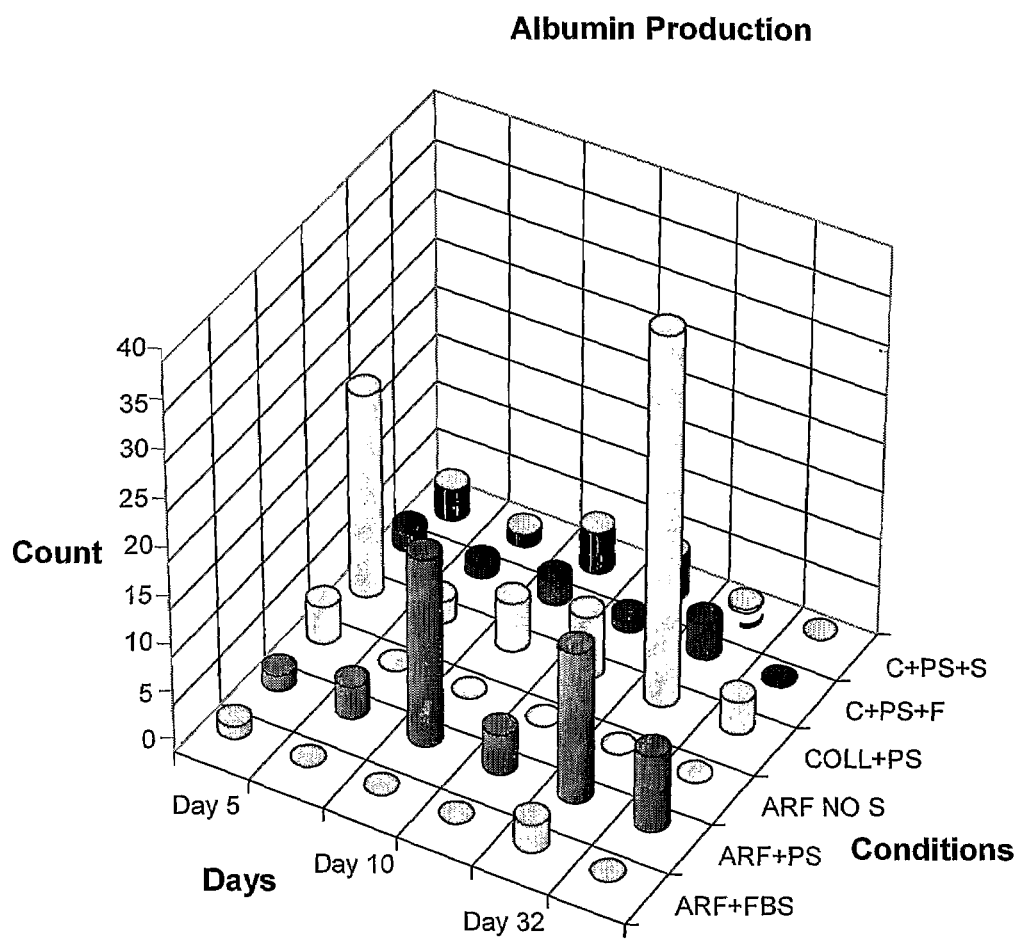
FIG. 2 depicts a graph of albumin production by hepatocyte preparations as described in Example 2.1 herein, wherein ARF+FBS indicates hepatocytes grown in the presence of mitomycin arrested fibroblasts (ARF) in media supplemented with 10% fetal bovine serum (FBS), ARF+PS indicates hepatocytes grown in the presence of ARF in media supplemented with 10% porcine serum (PS), ARF NO S indicates hepatocytes grown in the presence of ARF in serum-free media, COLL+PS indicates hepatocytes grown in collagen coated flasks in media supplemented with 10% PS, C+PS+F indicates hepatocytes grown in collagen (C) coated flasks in media supplemented with 5% PS and 5% fibroblast-conditioned growth media (F), C+PS+S indicates hepatocytes grown in collagen coated flasks in media supplemented with 5% PS and 5% Sertoli-conditioned growth media (S)

As show in FIG. 2, the highest albumin production was observed in cultures supplemented with porcine serum (PS). Hepatocytes grown in media supplemented with PS on arrested fibroblasts yielded a maximum albumin release of 19.5 µg/ml for 4 hours at day 10 in culture (see FIG. 2). Hepatocytes grown on collagen matrix in GM supplemented with PS showed a maximum albumin release at day 32 in culture of 38.3 µg/ml for 4 hours.

Maximum albumin production for hepatocytes grown in GM supplemented with PS and with fibroblast-conditioned growth media was 3.76 µg/ml at day 32 of culture. Maximum albumin production of hepatocytes grown in GM supplemented with PS and Sertoli-conditioned growth media was 4.56 µg/ml at day 13 in culture.

These results demonstrate that hepatocyte unction, as assessed by albumin production was best maintained when the hepatocytes were grown in collagen coated flasks in growth media supplemented with 10% PS. A liver cell-extra-cellular matrix interaction and the presence of allogeneic serum are important for the maintenance of a liver cell phenotype in long term tissue culture. It is expected that similar conditions will produce maximum liver secretory factors in non-hepatocyte cell cultures according to the invention.

In another experiment, liver cells were isolated from male and female large White/Landrace cross neonatal pigs according to the method described above. Cells were seeded at a density of $2\times10^6$ viable cells in 25 cm collagen-coated flasks (Sigma, USA) and were maintained at 37° C. in a humidified incubator in an atmosphere of 95% air and 5% $CO_2$. Cells were cultured in DMEM/F12 media, and 10% porcine serum. After 48 hours the cells were rinsed with PBS and fresh culture media was added. Fresh media was subsequently added every 2-3 days as needed.

Functional tests to measure albumin release and Factor VIII release were performed at 1, 2, and 3 weeks as described above. Cell numbers and viability was also determined. The viability of the porcine cells was excellent (>90%) at all time points tested using the current methods (see Table 2.1). During the initial 24-48 hours post isolation the numbers of viable cells did decline (data not shown). However, the numbers of viable liver cells increased almost linearly from that point on until the conclusion of the studies 3 weeks later.

The maintenance of liver cell function of the isolated liver cells was confirmed using albumin and Factor VIII release. Both albumin and Factor VIII were detectable 1 week post isolation. Quantitative determinations demonstrated that, on a per cell basis, the release of both albumin and Factor VIII increased markedly from 1 to 3 weeks in culture (Table 2.1).

TABLE 2.1

In Vitro Characteristics of Isolated Neonatal Hepatocytes

| Time Post Isolation | Cell Viability % | Cell Number $10^6$ (proliferation) | Albumin Release (µg/ml) | Factor VIII Release (mU/ml) |
|---|---|---|---|---|
| 1 wk | 91.3 (90.0-93.0) | 0.25 (0.2-0.3) | 1.7 (0-2.8) | 1.1 (.03-1.9) |
| 2 wks | 89.8 (86.5-93.4) | 1.1 (0.9-1.4) | 11.6 (8.3-14.8) | 3.3 (2.4-3.1) |
| 3 wks | 89.2 (84.9-93.4) | 2.6 (2-3.25) | 29.4 (26.3-32.5) | 11.9 (11.3-13.4) |

Data for albumin and Factor VIII release are expressed as per 1 million cells.

2.2 Indocyanine Green Uptake

Indocyanine green (ICG) is a non-toxic organic anion that is used in clinical tests to evaluate liver function, as it is eliminated exclusively by hepatocytes in vivo. ICG uptake has been used to identify differentiated hepatocytes from stem cells in culture (Yamada et al., 2002). In the present study, cellular uptake of ICG was used to identify hepatocytes in culture in a screening method to identify the best culture conditions for the long term maintenance of hepatocyte function.

ICG was used at a concentration of 1 mg/ml dissolved in 5 ml sterile water and 20 ml DMEM with 10% PS. The ICG solution was added to the cell culture flask and incubated at 37° C. for 15 min. After the flask was rinsed three times with PBS, the cellular uptake of ICG was examined by microscopy. After the examination, the flask was refilled with fresh growth media.

Microscopic examination of isolated neonatal hepatocytes showed that approximately 50% of cells were ICG positive.

In another experiment, ICG uptake by neonatal porcine liver cells cultured in media supplemented with 10% PS in collagen-coated flasks was determined. After 3 weeks in culture, the percentage of ICG positive cells was very high and ranged between 80-90%. After 4 hours of incubation virtually all of the cells released the ICG that had been taken up, wherein said release is a marker for release after metabolism.

The maintenance of liver cell function in long term tissue culture can be readily assessed by ICG uptake. Furthermore, administration of ICG to liver cells in tissue culture is a useful methodology to manipulate liver cell function and control hepatocyte differentiation in vitro.

2.3 Secretory Function of Different Cell Types

The importance of the procedures used to isolate liver cells from tissue to the maintenance of liver cell function was assessed, using Factor VIII secretion and albumin production as markers for secretory liver cell function. The ability of non-parenchymal (NPC) cells from the liver, and epithelial and endothelial cells from gall bladder and liver vessels, to exhibit and maintain a secretory liver cell phenotype in culture was also assessed.

One neonatal (one week old) piglet, and one approximately 6 month old pig were used in the following experiments. The supernatant of cultured cells was harvested as indicated, and albumin release and Factor VIII functional tests (ELISA, and coagulation test as described herein, respectively) were performed. ICG uptake tests were also performed as indicated.

Hepatocytes were isolated from one neonatal pig liver following our standard procedure described herein, with two rounds of digestion with Liberase® (0.2 mg/ml) for 10 min. After isolation, cells were counted and plated in 25 cm² flasks, with 4.5×10⁶ cells/flask. Cells were counted after 5 days in culture, and viability was checked by trypan blue exclusion as described above. Albumin and Factor VIII release were assessed at day 5 in culture.

The production of Factor VIII was measured using a Factor VIII coagulation assay (Coatest VIII:C/4 from Chromogenix) according to the manufacturer's protocol. Percent values for the rate of Factor VIII coagulation are relative to the rate of Factor VIII coagulation at normal blood levels of Factor VIII.

37×10⁶ hepatocytes were isolated from one neonatal pig liver as described above. Viability of the cells immediately after isolation was 98%. After 5 days in culture, cell survival rate averaged 60%. Albumin production after 5 days in culture was 4.45 ug/ml/4 h. The maximal rate of Factor VIII coagulation was 0.2%. Staining with ICG was used to identify the percentage of hepatocytes in cell culture. 43% of cells were ICG positive in normal liver preparation after 4 weeks in culture.

Non-parenchymal liver cells (NPC) were isolated from the same liver used for hepatocyte isolation. Cell yield was low, as expected from previous reports (Gerlach, 2001). Despite this, NPC so isolated were competent to produce Factor VIII, and indeed were producing approximately the same amount of Factor VIII as hepatocytes (approximately 0.2%) with about one-third the amount of cells.

Epithelial and endothelial cells from piglet gall bladder and liver vessels were isolated. These cells showed good growth in culture, proliferated under the culture conditions used, and exhibited the highest rate of Factor VIII coagulation, at 3.7%.

2.4 Proliferation of Hepatocytes and Maintenance of Function in Long Term Cultures The effects of cell isolation methodology and culture conditions on cell proliferation and secretory function were assessed.

Cell proliferation: Neonatal hepatocytes were isolated according to our standard method described herein. 250,000 cells were seeded in flasks, and cultured in growth media supplemented with 10% FBS. Proliferation of cells in culture was determined at 1 day in culture, 7 days in culture, 14 days in culture, and 21 days in culture.

The number of viable cells, relative to day 1 of culture, in growth media supplemented with 10% FBS was 20% at day 7, 203% at day 14, and 287% at day 21.

Albumin release: Hepatocytes in growth media supplemented with 10% PS or 10% FBS were cultured, and albumin release was checked as described above at 1, 2, 3, 7, 8, and 9 weeks of culture. Pig fibroblasts in growth media supplemented with 10% PS or 10% FBS were used as a negative control.

Figure 3:
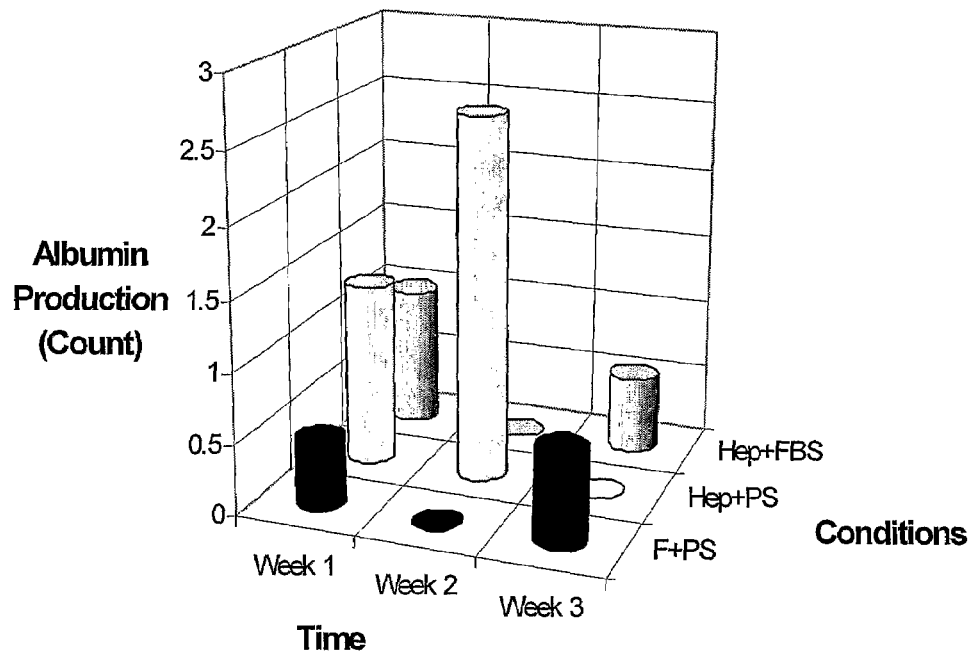
FIG. 3 depicts a graph presenting albumin production by fibroblasts in growth medium supplemented with porcine serum (F+PS), hepatocytes in growth media supplemented with porcine serum (Hep+PS), hepatocytes in media supplemented with foetal bovine serum (Hep+FBS), as described in Example 2.4 herein.

Maximum albumin release for hepatocytes cultured in growth media supplemented with 10% porcine serum was observed at week 9 (19.1 µg/ml for 4 hours). A rise in albumin production was observed in the negative control, with a maximum albumin release of 0.67 µg/ml at week 3 (see FIG. 3).

The low cell viability at day 7 of culture indicated that the hepatocytes were damaged during the isolation step. However, under these conditions the hepatocytes were able to recover and proliferate.

Albumin production was inhibited for several weeks in culture with albumin release considerably lower than that described elsewhere herein. Again however, under these culture conditions liver cell function recovered after 8-9 weeks in culture.

Hepatocytes isolated and cultured as described can be successfully cultured to maintain hepatocyte function, including liver hepatocyte secretory functions for at least 9 weeks ex vivo.

2.5 Immunoperoxidase Cell Characterization

An immunoperoxidase method to distinguish different liver cell populations in culture was developed. Adult pig and neonatal pig livers were stained with hepatocyte specific antigen and for von Willebrand factor to distinguish endothelial cells and hepatocytes. The following markers were used: hepatocyte antigen and cytokeratin for mature hepatocytes; von Willebrand factor for endothelial cells; vimentin for cells of mesenchymal origin; and Factor VIII to identify cells that are the main producers of the factor.

Freshly isolated liver cells or tissues were formalin fixed, paraffin embedded, and sectioned at 2 µm, Unstained slides were deparaffinized in xylene and hydrated in graded alcohols. Slides were treated with 0.5% $H_2O_2$ for 5 min to block endogenous peroxidase activity. Sections were stained with primary antibody using the DAKO EnVision System according to the manufacturer's protocol. Sections were incubated for 30 min with primary antibody, followed by 30 min incubation with peroxidase-labelled polymer, and 5 min incubation with substrate-chromogen. Slides were counterstained with hematoxylin.

The following Table summarises the characteristics of the cell populations.

TABLE 2.2

Characterization of Cell Type

| Cell Type | Hepatocytes | Gall Bladder Epithelial cells | Endothelial cells from liver vessels | NPC from liver |
|---|---|---|---|---|
| Albumin secretion | Positive | Positive | Positive | Positive |
| Factor VIII secretion | Positive | Positive | Positive | Positive |
| ICG Uptake | 60-95% Positive | <1% Positive | <1% Positive | <30% Positive |
| Immunoperoxidase Markers | | | | |

TABLE 2.2-continued

Characterization of Cell Type

| Cell Type | Hepatocytes | Gall Bladder Epithelial cells | Endothelial cells from liver vessels | NPC from liver |
|---|---|---|---|---|
| Alpha feotoprotein | Positive | Negative | Negative | Negative |
| Cytokeratin CK 7 | Negative | 10% Positive | Negative | Negative |
| Vimentin | Negative | Negative | Positive | Positive |

NPC = Non parenchymal liver cells 2.6 Co-Culture of Secretory Cell with Companion Cells The applicant has co-cultured various combinations of non-hepatocyte cells and hepatocyte cells and studied the effects on Factor VIII production. The data summarised in Table 2.3 shows that Factor VIII secretion is generally markedly increased in co-cultures of non-hepatocytes with hepatocyte cells.

TABLE 2.3

Effect of Co-culturing on Factor VIII secretion

| Tissue or Cell Associations in Co-culture | FVIII Released µU/ml |
|---|---|
| Experiment A | |
| Lung Tissue | <0.1 |
| Lung Tissue + Hepatocytes (0.5 × 10$^6$ cells) | 0.35 |
| Gall Bladder Epithelial (10$^6$ cells) | 1.02 |
| Gall Bladder Epithelial (10$^6$ cells) + Hepatocytes (0.5 × 10$^6$ cells) | 0.48 |
| Endothelial (10$^6$ cells) | <0.1 |
| Endothelial (10$^6$ cells) + Hepatocytes (0.5 × 10$^6$ cells) | 0.97 |
| Hepatocytes (10$^6$ cells) | 0.58 |
| Experiment B | |
| Gall Bladder Epithelial (0.5 × 10$^6$ cells) | 0.65 |
| Gall Bladder Epithelial (0.5 × 10$^6$ cells) + Hepatocytes (0.5 × 10$^6$ cells) | 1.15 |
| Gall Bladder Epithelial (0.5 × 10$^6$ cells) + Hepatocytes (1.0 × 10$^6$ cells) | 0.94 |
| Gall Bladder Epithelial (0.5 × 10$^6$ cells) + Hepatocytes (1.5 × 10$^6$ cells) | 1.22 |
| Endothelial (10$^6$ cells) | 0.15 |
| Endothelial (10$^6$ cells) + Hepatocytes (100,000 cells) | 0.68 |
| Hepatocytes (1 × 10$^6$ cells) | 0.64 |

EXAMPLE 3

Cryopreservation of Hepatocytes

Hepatocytes were isolated according to our standard procedure described above, and additionally according to our modified procedure, in which digestion with Liberase® during isolation is performed in media supplemented with PS. The isolated hepatocytes were pooled, and then frozen following the standard procedure described under the following three different conditions: in 10% DMSO in FBS; 10% FBS and 10% DMSO in GM; and 10% DMSO in PS. Cells were stored in liquid nitrogen. After one week and three weeks storage, cells were defrosted and viability and recovery were determined, Results are summarised in Table 3.1.

Cells maintained good viability and recovery after storage in liquid nitrogen for one to two weeks. The best viability and recovery of cryopreserved hepatocytes was observed with hepatocytes isolated according to our modified procedure and frozen in 10% DMSO in PS. It is expected that non-hepatocyte cells will also be viable and able to be cultured after being stored frozen as described above for hepatocytes.

TABLE 3.1

Hepatocyte cryopreservation

| | | Cells cultured for 3 days | | Cells cultured for 30 days | |
|---|---|---|---|---|---|
| | Viability | Viability | Recovery | Viability | Recovery |
| PS/DMSO Modified isolation | 96% | 83% | 72% | 80% | 60% |
| GM/DMSO | 96% | 60% | 43% | 76% | 30% |
| FBS/DMSO Modified isolation | 96% | 81% | 64% | ND | ND |
| PS/DMSO Conventional isolation | 57% | 61% | 45% | 0% | 0% |

Viability is the percentage of living cells. Recovery is the percentage of living cells after thawing. ND = Not Determined.

EXAMPLE 4

Ischaemia During Cell Isolation

The effect of different modes of ischemia during cell isolation and of the isolation methodology itself on liver cell function and the maintenance of liver cell function was assessed as follows.

4.1 Cold Ischemia

The effect of cold ischemia during cell isolation on liver cell function were assessed as follows. Liver was cut into small pieces, and put in a large volume of cold DMEM for 24 hours storage at 4° C. Hepatocytes and NPC were then isolated following the standard procedure as described herein.

Figure 4:
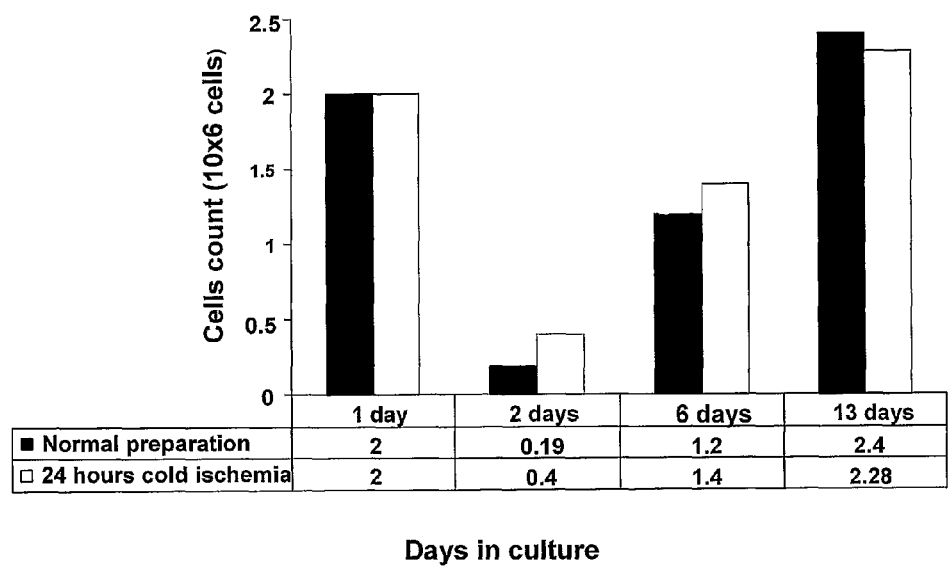
FIG. 4 depicts a graph presenting cell counts of hepatocytes isolated by our standard procedure and by the cold ischemia method, as described in Example 4 herein.

251×10$^6$ hepatocytes were isolated from one pig liver using the cold ischemia method described above. Viability immediately after isolation was 21%, with 52×10$^6$ cells surviving isolation. The number of viable cells isolated using the standard procedure and using cold ischemia was not significantly different (see FIG. 4).

444×10$^6$ non parenchymal cells (NPC) were isolated from the same liver. Viability immediately after isolation was 6.3%. After isolation using the cold ischemia procedure, 95% of cells in culture were positive for ICG.

Figure 5:
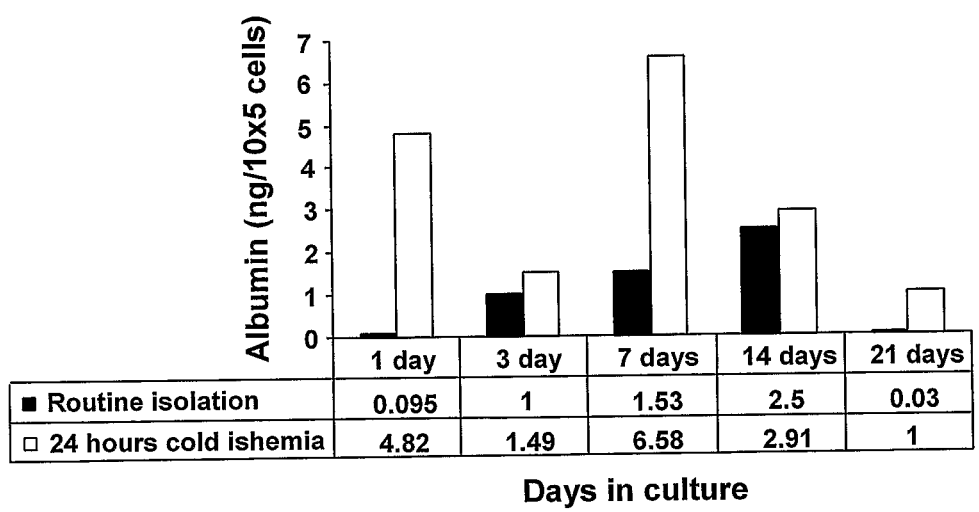
FIG. 5 depicts a graph presenting albumin production by hepatocytes isolated by our standard procedure and by the cold ischemia method, as described in Example 4 herein.
Figure 6:
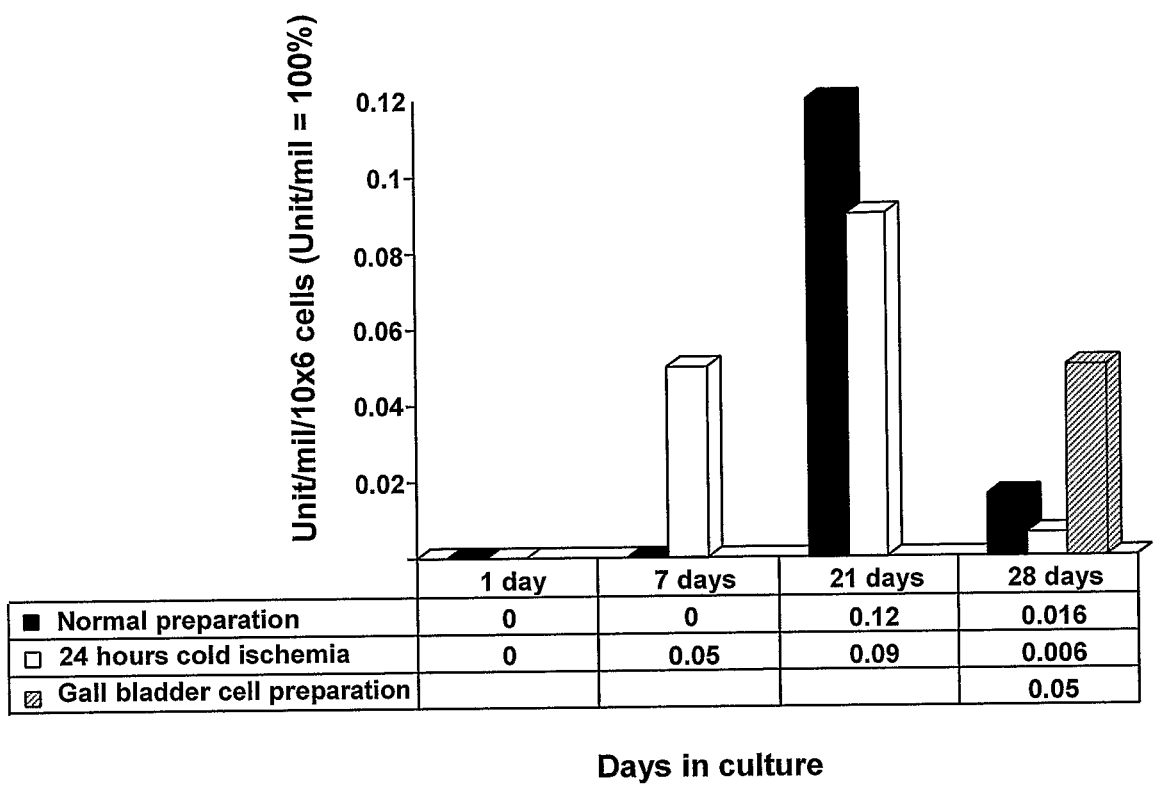
FIG. 6 depicts a graph presenting factor VIII production by hepatocytes isolated by our standard procedure and by the cold ischemia method, and by gall bladder cells, as described in Example 4 herein.

Regarding Factor VIII and albumin secretion, the hepatocytes isolated using the cold ischemia method secreted significantly more albumin at all time points than cells prepared by the standard procedure (see FIG. 5). Factor VIII production was variable but was significantly lighter in hepatocytes produced by cold ischemia after 1 and 7 days (see FIG. 6).

The Applicants believe, without wishing to be bound by theory, that ischemia during isolation may result in a more robust and virile hepatocyte and non-hepatocyte population in which hepatocyte secretory liver cell function is maintained in long-term culture.

4.2 Isolation of Epithelial and Endothelial Cells

Epithelial and endothelial cells were isolated from pig gall bladder and liver vessels as follows. Briefly, gall bladder was thoroughly washed with sterile DMEM to remove bile, cut in pieces, and digested for 30 min Liberase® solution (with 0.2 mg/ml). Cells were then washed with DMEM tree times. Cell count and viability tests were performed immediately after isolation, and at day 7, day 16, and day 28 in culture. Cells were plated at 15×10⁶/flask in 25 cm² flasks, Considerable Factor VIII release by epithelial and endothelial cells isolated from pig gall bladder was observed after 4 weeks in culture (see FIG. 6).

Cells isolated from liver vessels also showed considerable amount of Factor VIII release after 4 weeks in culture (not shown).

In summary, the standard isolation technique using low Liberase® concentration provides good results with respect to cell yield and viability. In this instance, the viability of cells isolated using the Applicant's cold ischemia protocol was comparable to that achieved using the standard method. However, these non-hepatocyte cells cultured following cold ischemia isolation showed better functional recovery compared to those isolated by the standard procedure, as demonstrated by higher albumin release.

Irrespective of the isolation method used, the cultured cells maintained liver factor secretory function in culture. The applicant's data shows that epithelial and endothelial cells isolated from pig gall bladder and liver vessels secrete Factor VIII in culture, in excess of that observed at the same timepoint with hepatocytes.

EXAMPLE 5

Encapsulation of Non-Hepatocyte Cell and/or Hepatocytes

Methods to encapsulate non-hepatocyte cells and/or hepatocytes as single cells and as cell clusters were developed.

Cells isolated from pig gall bladder and liver vessels as well as hepatocytes (as described above) may be encapsulated using 1.5% alginate for the formation of capsules by known methods (WO 01/52871).

Single cells and cell clusters can be encapsulated, and the integrity of capsules verified by microscopy. For both single cells and cell clusters, no cells should be embedded in the capsule wall, and capsules of even shape and size, approximately (200 µm in diameter) are preferred.

Encapsulation of mouse hepatocytes in alginate (1.5%) resulted in capsules of good shape and integrity, with no cells embedded in the capsule walls, indicating that liver cells from mammals other than pigs are amenable to aggregate formation and/or encapsulation.

EXAMPLE 6

Transplantation

Two modes of non-hepatocyte cell transplant delivery have been considered; alginate encapsulation, and incorporation into the TheraCyte device. It is considered that such devices will allow the cells to maintain liver factor secretory function and allow release of Factor VIII both in vitro and in vivo.

Alginate Encapsulation

Non-Hepatocytes can be encapsulated in alginate using different alginate concentrations (1.5%, 1.6%, and 1.7%) to form capsules by known methods. Encapsulation using polyornithine (PLO) or polylysine (PLL) coating to improve capsule integrity and Factor VIII release may also be used. Additionally, both single cells and cell clusters can be encapsulated.

Capsules with single non-hepatocytes or cell clusters can be transplanted into host animals. Capsules containing hepatocytes remained viable after 3 weeks transplanted in CD1 mice. It is expected that capsules containing non-hepatocyte cells would also remain viable for similar time periods. Cell viability can be checked by trypan blue and acridine orange/propidium iodate staining. Approximately 65% of the retrieved hepatocyte cells were ICG positive indicating that the majority of retrieved cells were mature hepatocytes.

Incorporation into TheraCyte Device

One million hepatocytes and/or non-hepatocyte cells can be loaded into a TheraCyte™ device. For in vitro analysis the TheraCyte™ device can be maintained in vitro in culture media supplemented as described above with 10% allogeneic serum. Albumin and Factor VIII release from the TheraCyte™ maintained in vitro can then be measured. Factor VIII coagulation assays can be carried out to check that Factor VIII is being released from the TheraCyte™ device in amounts comparable to that released when free in culture.

To test for in vivo efficacy, the TheraCyte™ device can be transplanted subcutaneously in a host animal. The TheraCyte™ device can be retrieved and cell viability measured as above. Histological studies would also be useful to confirm that there is no inflammatory reaction in the tissues surrounding the transplantation site.

In one experiment, the survival and maintenance of hepatocyte cell function of neonatal porcine liver cells following transplantation into a xenogeneic host was determined. After isolation using the cold ischemia step described above, neonatal porcine liver cells were cultured in media supplemented with 10% PS in collagen-coated flasks. Cells were removed from the flasks using Protease (TrypLE Select, Gibco, USA) and were briefly rinsed in 3 ml of PBS. Cells were then suspended at a concentration of 1×10⁶/20 µl and loaded into 20 µl immunoisolatory 20 µl Theracyte™ devices using standard procedures as detailed by the manufacturer. CD1 mice (N=3) were anesthetized using Halothane (2%) and a small 1 cm incision was made in the abdomen. The device was carefully placed overlying the liver and the incision was sutured closed. All procedures were performed using sterile techniques. Eight weeks later, the devices were removed from the animals for determinations of cell viability. One device was removed and immediately fixed in 10% buffered formalin. The device was embedded in paraffin and 3 µM thick microtome sections were stained for hematoxylin and eosin (H&E). The remaining 2 devices were removed and cut open to flush the encapsulated cells from the device for viability determinations and ICG analysis.

The Theracyte™ devices were well-tolerated in all of the transplanted animals. All three mice remained extremely healthy and vigorous during the 8 week transplant period. Post-mortem analysis did not reveal any signs of inflammation as the peritoneal surfaces appeared normal, pale and glistening. As anticipated, the devices were slightly adhered to the surrounding organs including the liver but were removed with little disturbance of the surrounding tissue/vasculature.

H&E-stained sections of a retrieved device at 8 weeks supported the biocompatibility of the devices after 8 weeks in the intraperitoneal cavity The tissue adherent to the Theracyte™ devices involved organised fibrous tissue. There was notable absence of any acute inflammatory cell reaction, and absence of pronounced round cell infiltrate. Within the device there were numerous, well defined clumps of viable liver cells randomly distributed throughout the lumen. The liver cells were removed from the remaining 2 cell-loaded devices and tested for viability and function using the ICG test described above. There was no diminishment in the numbers of viable/functional cells relative to pre-transplant values as the proportion of ICG-positive cells was 80-90% after 8 weeks in vivo. Further analysis using trypan blue exclusion confirmed that approximately 90% of the retrieved cells were viable.

The above studies show that liver cell viability, function, and phenotype can be maintained for extended periods in transplanted alginate capsules and transplantation devices such as the TheraCyte™ device. Additionally, the transplanted liver cells do not provoke an immune reaction and are immunologically isolated from the recipient. It is expected that the transplantation of non-hepatocyte cells will prove equally efficacious.

Figure 7:
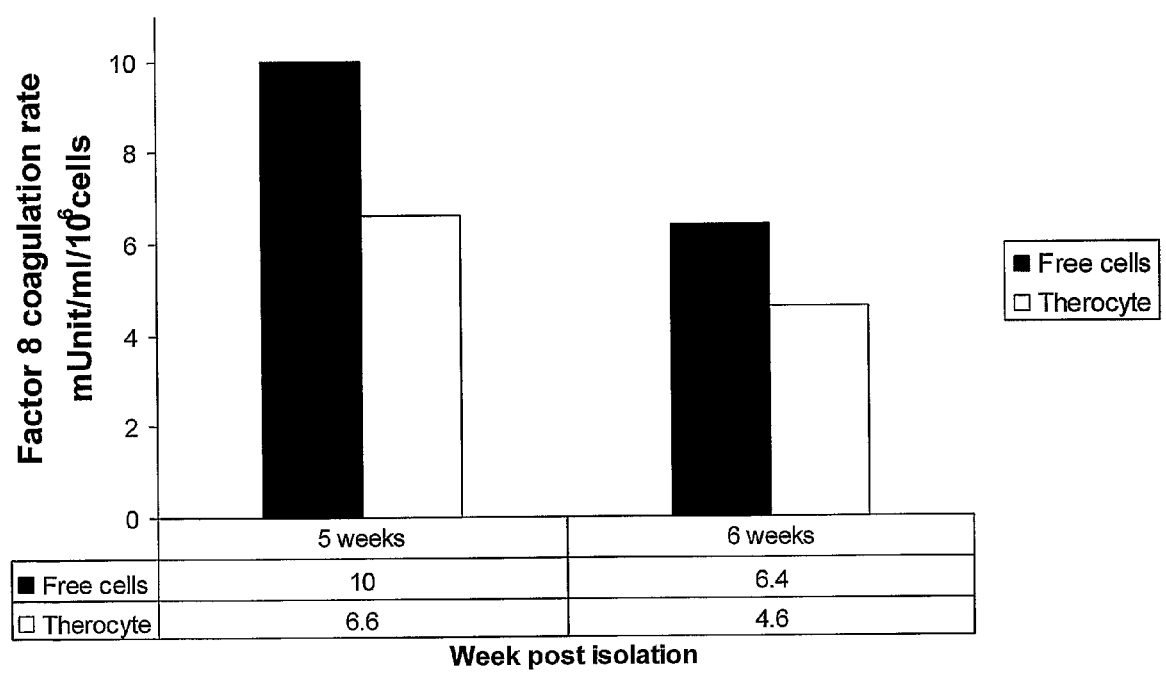
FIG. 7 shows albumin release from hepatocytes incorporated into a TheraCyte device maintained in vitro, as described in Example 6 herein.
Figure 8:
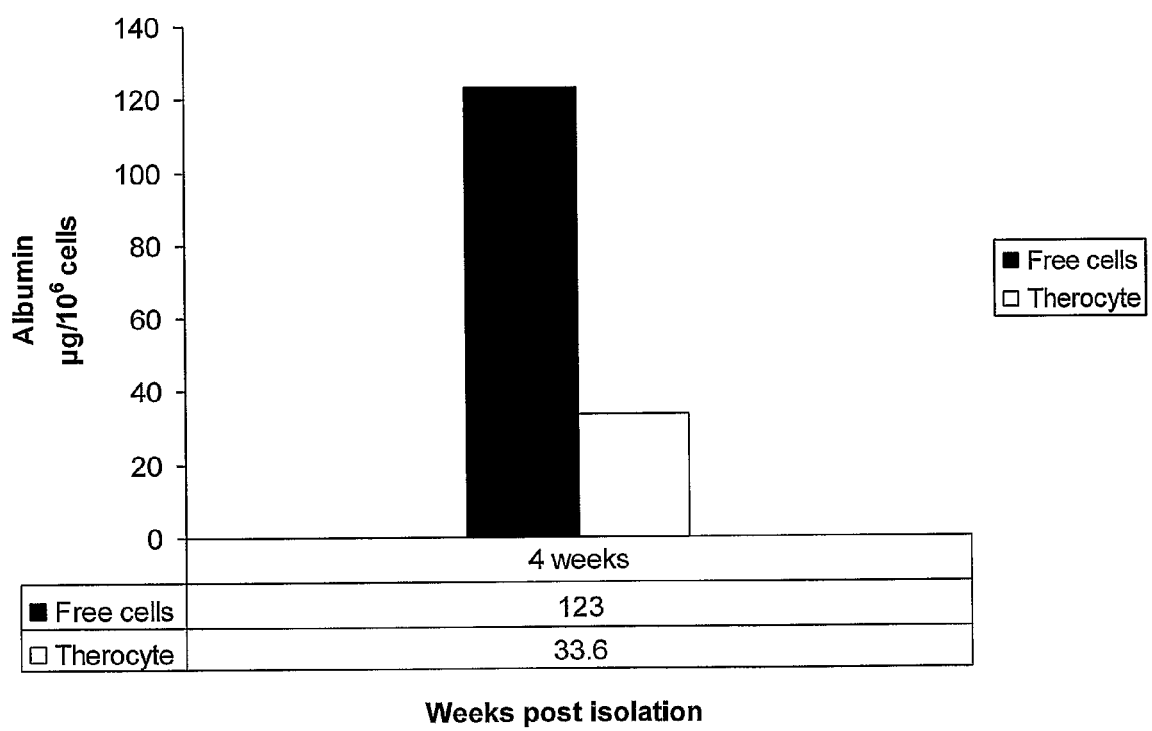
FIG. 8 shows Factor VIII release from hepatocytes incorporated into a TheraCyte device maintained in vitro, as described in Example 6 herein.

The hepatocyte loaded TheraCyte™ devices were also tested in vitro in culture supplemented with 10% PS and albumin and Factor VII release from the TheraCyte™ device measured. The results showed that the TheraCyte™ device released albumin and Factor VIII for up to six weeks (see FIGS. 7 and 8). Whilst the factors secreted were less than that secreted by free cells in culture, they were nevertheless secreted at a physiologically effective amount (FIGS. 7 and 8).

EXAMPLE 7

Effective Encapsulated Pig Cells Transplanted into Hemophiliac Mice

A colony of Factor VIII deficient mice was bred at Brown University with a Black/6:129 mixed background, While this strain still produced Factor VIII in normal amounts, it is biologically inactive due to a point mutation in the protein.

Porcine neonatal and adult hepatocyte cells were isolated using the cold ischemia procedure described above and prepared and cultured according to the invention. All neonatal cells or adult cells were diluted to a concentration of 5 million cells/ml and encapsulated into Medipol alginate under standard PLO coating conditions.

Empty capsules were made the same way. Capsules were held in vitro for 3 days, washed in serum media and HBSS, and implanted into the IP cavity of mice. A midline abdominal incision was made roughly 5-8 mm in length and a sterile 2 mL serologic pipette was used to introduce 400 μL of capsules suspended in 600 μL HBSS for a total of 2 million cells in 1 mL delivery vehicle.

The incision and underlying muscles were closed separately with 8-0 nylon. Tails were bled under controlled conditions for 5 minutes into eppendorf tubes spiked with citrate. In this study, blood volume was quantified using a micropipette instead of the blood lysis assay.

Figure 9:
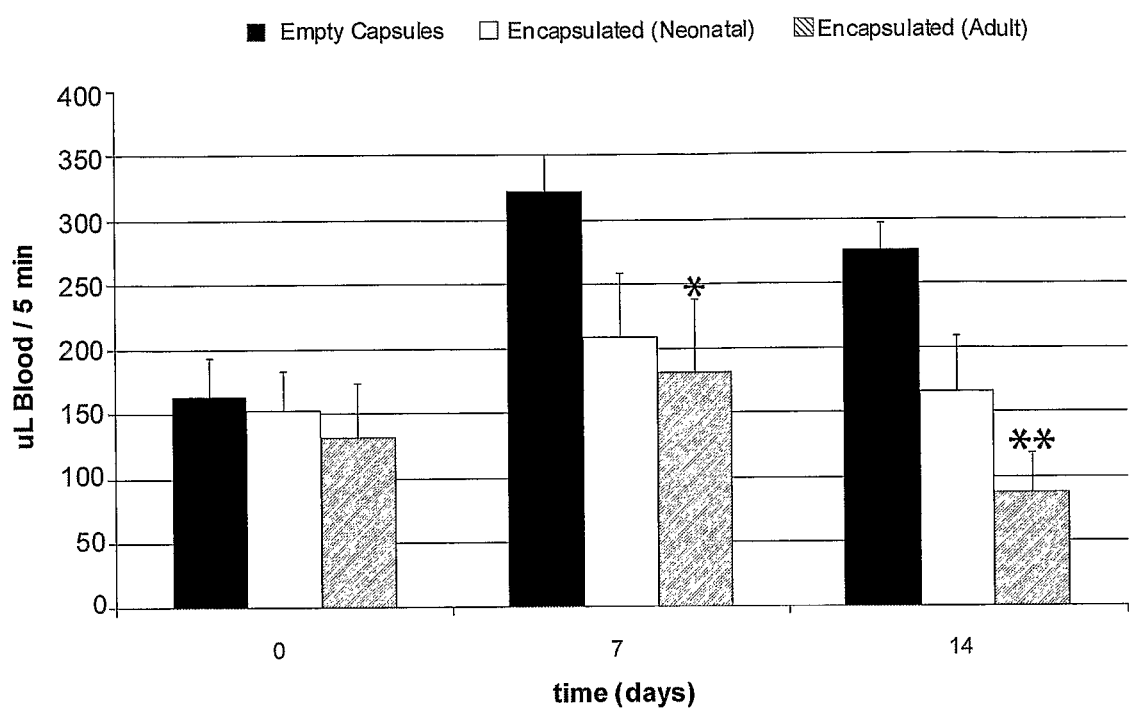
FIG. 9 shows the effect of encapsulated pig cells transplanted in haemophiliac mice.

The therapeutic effect of encapsulated hepatocytes was seen at 7 and 14 days post implantation, when compared to control bleeding rates. Whilst the one week bleeding volume increased from day 0, this phenomenon was observed throughout the study and may be due to the hypervascularization associated with repeated injury to the tail and thus more effective bleeding over time. However, the results, shown in FIG. 9, demonstrate Factor VIII activity up to two weeks. Both encapsulated groups show reduced bleeding compared to the control, Industrial Application The present invention is directed to pharmaceutical compositions for treating liver disease and disorders. The compositions comprise at least one non-hepatocyte cell type selected from the group consisting of gall bladder epithelial cells, gall bladder endothelial cells, bile duct epithelial cells, bile duct endothelial cells, hepatic vessel epithelial cells, hepatic vessel endothelial cells, sinusoid cells and non-parenchymal liver cells which are capable upon transplantation into a recipient host of secreting Factor VIII and other liver secretory factors. Devices comprising the compositions for implantation into a recipient host are also provided. Long term in vitro culture methods for hepatocytes and for said non-hepatocyte cell type are also provided. The composition may additionally comprise hepatocytes.

All patents, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of various embodiments or preferred embodiments and are exemplary only and not intended as limitations on the scope of the invention. Other objects, aspects, examples and embodiments will occur to those skilled in the art upon consideration of his specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the at, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims, In addition, where features or aspects of the invention are described in terms of Markush groups, those skilled in the art will recognize that the invention is also thereby described in terms of any individual member or subgroup of members of the Markush group.

What we claim is:

1. An implantable composition comprising hepatocyte cells and at least one neonatal non-hepatocyte cell, said neonatal non-hepatocyte cell being capable upon implantation into a recipient of secreting one or more liver secretory factors or of providing one or more liver metabolic and/or physiologic functions to said recipient, wherein said composition comprises cells or aggregates thereof, wherein said neonatal non-hepatocyte cell is selected from the group consisting of gall bladder epithelial cells and gall bladder endothelial cells, wherein said non-hepatocyte cell maintains its secretory phenotype, and wherein the ratio of hepatocyte cell number to non-hepatocyte cell number is between 0.5:2 and 2:0.5.

2. The composition of claim 1, wherein the at least one neonatal non-hepatocyte cell is a pig or human cell.

3. The composition of claim 1, comprising gall bladder epithelial cells.

4. The composition of claim 1 wherein there is a ratio of epithelial cell number to hepatocyte cell number of 1:1.

5. The composition of claim 1, wherein the one or more liver secretory factors is a blood clotting factor.

6. The composition of claim 1, wherein the one or more liver secretor factors is Factor VIII and/or Factor IX.

7. The composition of claim 1, wherein the one or more liver secretory factors is Factor VIII, and von Willebrand factor.

8. The composition of claim 1, wherein the one or more liver secretory factors is a growth and/or differentiation factor.

9. The composition of claim 1, wherein the one or more liver secretory factors is an enzyme.

10. The composition of claim 1, wherein said neonatal non-hepatocyte cells are derived from the same species as the recipient.

11. A device for implantation into a recipient suffering from or predisposed to a disease associated with a deficiency in or absence of a secreted liver factor, the device comprising the implantable composition of claim 1.

12. A device for implantation into a recipient suffering from or predisposed to a disease associated with a deficiency in or absence of a secreted liver factor, the device comprising
 (i) a capsule comprising a suitable biocompatible material; or
 (ii) a vascularized tube or chamber; or
 (iii) a subcutaneous implant device which is impermeable to cells but permeable to proteins and secreted factors; or
 (iv) a matrix preparation comprising gelatin, collagen, or natural carbohydrate polymers or a plasma thrombin clot; and
 (v) one or more implantable compositions comprising hepatocytes and at least one neonatal non-hepatocyte cell, wherein said neonatal non-hepatocyte cell is capable, upon implantation into a recipient, of secreting one or more liver secretory factors or of providing one or more liver metabolic and/or physiologic functions to said recipient, wherein said composition comprises cells or aggregates thereof, wherein said at least one neonatal non-hepatocyte cell is selected from the group consisting of gall bladder epithelial cells and gall bladder endothelial cells, wherein said neonatal non-hepatocyte cell maintains its secretory phenotype, and wherein there is a ratio of hepatocyte cell number to non-hepatocyte cell number between 0.5:2 and 2:0.5 in said one or more implantable compositions.

13. The device of claim 12, wherein the hepatocytes are isolated from immortalized cells.

14. The device of claim 12, wherein the biocompatible material is alginate.

15. The device of claim 12, wherein the plasma thrombin clot is an allogeneic plasma clot produced with allogeneic thrombin.

16. A method of producing one or more liver secretory factors in vivo, comprising the step of implanting an effective amount of the implantable composition as claimed in claim 1 into a patient in need thereof.

17. The method of claim 16, wherein said composition provides liver secretory factors or provides liver metabolic or physiologic functions over an extended period post implantation.

18. A method of treating a patient suffering from or predisposed to a disease or condition associated with a deficiency in or absence of a liver secreted factor comprising the implantation of an effective amount of the implantable composition of claim 1 to a patient in need thereof.

19. The method of claim 18, wherein said disease or condition is selected from the group of diseases consisting of chronic liver insufficiency, liver failure, liver disease and alcoholic liver disease.

20. The method of claim 18, wherein said disease or condition is caused by infection with hepatitis A or B virus.

21. The method of claim 18, wherein the disease or condition is a blood clotting disease or condition.

22. The method of claim 21, wherein the blood clotting disease or condition is a hemophilia.

23. The method of claim 22, wherein said hemophilia is hemophilia A.

24. The method of claim 18, wherein the implantable composition comprises cells encapsulated in a suitable biocompatible material including alginate; cells confined in a vascularized tube or encapsulation device; cells encapsulated in matrix preparations including gelatin, collagen, or natural carbohydrate polymers; and/or cells confined in a plasma thrombin clot including allogeneic plasma clots produced with allogeneic thrombin.

25. A method of administering a blood clotting factor to a patient in need thereof, wherein said blood clotting factor is complexed and/or associated with one or more factors capable of enhancing the activity, stability, bioavailability, and/or efficacy of said blood clotting factor, wherein the method comprises the implantation of an effective amount of the implantable composition of claim 1 to said patient, wherein the blood clotting factor is Factor VIII, and said one or more factors capable of enhancing the activity, stability, bioavailability, and/or efficacy of said blood clotting factor is von Willebrand factor.

26. A method of treating a patient suffering from or predisposed to a disease or condition associated with a deficiency in a metabolic and/or physiologic function of the liver, said method comprising the implantation of an effective amount of the implantable composition of claim 1 to the patient.

27. The method of claim 26, wherein the disease or condition comprises chronic liver insufficiency, liver failure, liver disease, or alcoholic liver disease.

\* \* \* \* \*

UNITED STATES PATENT AND TRADEMARK OFFICE
CERTIFICATE OF CORRECTION

PATENT NO.        : 8,580,248 B2                              Page 1 of 1
APPLICATION NO. : 10/599518
DATED             : November 12, 2013
INVENTOR(S)       : Elliott et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1566 days.

Signed and Sealed this
Twenty-second Day of September, 2015

Michelle K. Lee
*Director of the United States Patent and Trademark Office*